(12) United States Patent
Tsotsos et al.

(10) Patent No.: US 12,115,416 B2
(45) Date of Patent: Oct. 15, 2024

(54) TRACKING REPETITIONS BY HEAD-MOUNTED DEVICE BASED ON DISTANCE

(71) Applicant: Google LLC, Mountain View, CA (US)

(72) Inventors: Konstantine Nicholas John Tsotsos, Corte Madera, CA (US); Ivo Duarte, Lisbon (PT); Joao Afonso, Mountain View, CA (US); Maria Nika Yocke, Redwood City, CA (US); Lucy Abramyan, Mountain View, CA (US); Luca Ballan, San Jose, CA (US); Christopher Ross, New York, NY (US); Young Hwan Kim, Mountain View, CA (US); José Carlos Maranhão Pascoal, Lisbon (PT)

(73) Assignee: Google LLC, Mountain View, CA (US)

( * ) Notice: Subject to any disclaimer, the term of this patent is extended or adjusted under 35 U.S.C. 154(b) by 251 days.

(21) Appl. No.: 17/654,327

(22) Filed: Mar. 10, 2022

(65) Prior Publication Data
US 2023/0285805 A1 Sep. 14, 2023

(51) Int. Cl.
*A63B 24/00* (2006.01)
*A63B 71/06* (2006.01)
*G06T 7/50* (2017.01)

(52) U.S. Cl.
CPC ...... *A63B 24/0062* (2013.01); *A63B 71/0622* (2013.01); *A63B 71/0686* (2013.01);
(Continued)

(58) Field of Classification Search
None
See application file for complete search history.

(56) References Cited

U.S. PATENT DOCUMENTS

| 11,861,055 B2 * | 1/2024 | Tanigawa | G06T 19/003 |
| 2015/0100141 A1 * | 4/2015 | Hughes | G06Q 10/0639 |
| | | | 700/92 |

(Continued)

FOREIGN PATENT DOCUMENTS

CN 109260667 A 1/2019

OTHER PUBLICATIONS

Alizadeh, "Object Distance Measurement Using a Single Camera for Robotic Applications", thesis, The Faculty of Graduate Studies, Laurentian University, Sep. 2, 2014, 126 pages.

(Continued)

*Primary Examiner* — Sunit Pandya
(74) *Attorney, Agent, or Firm* — Brake Hughes Bellermann LLP

(57) ABSTRACT

A method can include determining, by a head-mounted device based on first data received from a depth-sensing device included in the head-mounted device, that a first distance of the head-mounted device from a landmark is outside a completion range; outputting, based on the determination that the first distance of the head-mounted device from the landmark is outside the completion range from the landmark, an indication that a repetition has yet to be completed; determining, based on second data received from the depth-sensing device, that a second distance of head-mounted device from the landmark is within the completion range; and based on the determination that the second distance of the head-mounted device from the landmark is within the completion range, incrementing a repetition counter and outputting an indication that the repetition has been completed.

20 Claims, 11 Drawing Sheets

(52) U.S. Cl.
CPC ........ *G06T 7/50* (2017.01); *A63B 2024/0068* (2013.01); *A63B 2071/0666* (2013.01); *A63B 2220/05* (2013.01); *A63B 2220/13* (2013.01); *A63B 2220/17* (2013.01); *A63B 2220/20* (2013.01); *A63B 2220/30* (2013.01); *A63B 2220/40* (2013.01); *A63B 2220/62* (2013.01); *A63B 2220/836* (2013.01); *A63B 2230/62* (2013.01)

(56) References Cited

U.S. PATENT DOCUMENTS

| | | | |
|---|---|---|---|
| 2017/0262050 A1 | 9/2017 | Li | |
| 2019/0160339 A1* | 5/2019 | Zhang | G06V 40/23 |
| 2020/0206568 A1 | 7/2020 | Hong et al. | |
| 2021/0001172 A1* | 1/2021 | Namboodiri | G16H 20/30 |
| 2021/0097768 A1 | 4/2021 | Malia et al. | |
| 2021/0362029 A1 | 11/2021 | Koblin et al. | |

OTHER PUBLICATIONS

Scaramuzza, et al., "Visual-Inertial Odometry of Aerial Robots", Spring Encyclopedia of Robotics, 2019, 13 pages.
International Search Report and Written Opinion for PCT Application No. PCT/US2023/064120, mailed on Jun. 27, 2023, 17 pages.

\* cited by examiner

TRACKING REPETITIONS BY HEAD-MOUNTED DEVICE BASED ON DISTANCE

TECHNICAL FIELD

This description relates to exercise tracking.

BACKGROUND

Users may desire to perform exercises without having to personally count their repetitions.

SUMMARY

In some aspects, the techniques described herein relate to a method including: determining, by a head-mounted device based on first data received from a depth-sensing device included in the head-mounted device, that a first distance of the head-mounted device from a landmark is outside a completion range; outputting, based on the determination that the first distance of the head-mounted device from the landmark is outside the completion range from the landmark, an indication that a repetition has yet to be completed; determining, based on second data received from the depth-sensing device, that a second distance of head-mounted device from the landmark is within the completion range; and based on the determination that the second distance of the head-mounted device from the landmark is within the completion range, incrementing a repetition counter and outputting an indication that the repetition has been completed.

In some aspects, the techniques described herein relate to a method, further including determining the completion range based on a height of a user wearing the head-mounted device.

In some aspects, the techniques described herein relate to a method, further including determining the height of the user based on receiving input from the user.

In some aspects, the techniques described herein relate to a method, further including determining the height of the user based on third data received from the depth-sensing device while the user is in a standing position and orientation data received from a gyroscope.

In some aspects, the techniques described herein relate to a method, further including: determining an orientation range based on the first distance of the head-mounted device from the landmark; determining that an orientation of the head-mounted device is outside the orientation range based on orientation data received from a gyroscope; and based on the determination that the orientation of the head-mounted device is outside the orientation range, outputting an indication that a form of a user wearing the head-mounted device is incorrect.

In some aspects, the techniques described herein relate to a method, further including: determining an orientation range based on the first distance of the head-mounted device from the landmark; determining that an orientation of the head-mounted device is within the orientation range based on orientation data received from a gyroscope; and based on the determination that the orientation of the head-mounted device is within the orientation range, outputting an indication that a form of a user wearing the head-mounted device is correct.

In some aspects, the techniques described herein relate to a head-mounted device including: a depth-sensing device configured to capture determine distance; a gyroscope configured to determine an orientation of the head-mounted device; at least one processor; and a non-transitory computer-readable storage medium including instructions stored thereon that, when executed by the at least one processor, are configured to cause the head-mounted device to: based on the orientation of the head-mounted device being within a starting orientation range, output an instruction for a user to begin an exercise, the head-mounted device being disposed on a head of the user; determine, based on first data captured by the depth-sensing device, that a first distance of the head-mounted device from a landmark is outside a completion range; based on the first distance from the landmark being outside the completion range, output an instruction for the user to complete a first portion of the exercise; determine, based on second data captured by the depth-sensing device, that a second distance of the head-mounted device from the landmark is within the completion range; based on the second distance of the head-mounted device from the landmark being within the completion range, output an instruction for the user to perform a second portion of the exercise; determine, based on third data captured by the depth-sensing device, that a third distance of the head-mounted device from the landmark is within a starting position range; and based on the third distance of the head-mounted device from the landmark being within the starting position range, increment a repetition counter.

In some aspects, the techniques described herein relate to a head-mounted device, wherein the instructions are further configured to cause the head-mounted device to, before determining that the first distance of the head-mounted device from the landmark is outside the completion range: determine, based on fourth data captured by the depth-sensing device, that a third distance of the head-mounted device from the landmark is within the starting position range; and based on the determination that the third distance of the head-mounted device from the landmark is within the starting position range, set the repetition counter to zero.

In some aspects, the techniques described herein relate to a head-mounted device, wherein the instructions are further configured to cause the head-mounted device to, after outputting the instruction for the user to begin the exercise: run a timer while the third distance of the head-mounted device from the landmark is within the starting position range; and output a value of the timer.

In some aspects, the techniques described herein relate to a head-mounted device, wherein the instructions are further configured to cause the head-mounted device to, after outputting the instruction for the user to begin the exercise: determine that the orientation of the head-mounted device is outside a proper form range, the proper form range being based on the first distance of the head-mounted device from the landmark; and based on the determination that the orientation of the head-mounted device is outside the proper form range, output an instruction for the user to correct a body posture of the user.

In some aspects, the techniques described herein relate to a head-mounted device, wherein the completion range is based on a height of the user.

In some aspects, the techniques described herein relate to a head-mounted device, wherein the instructions are further configured to cause the head-mounted device to, before outputting the instruction for the user to begin the exercise, determine the height of the user based on fourth data captured by the depth-sensing device.

In some aspects, the techniques described herein relate to a head-mounted device, wherein the completion range is based on a height of the user and a category of the exercise.

In some aspects, the techniques described herein relate to a head-mounted device, wherein: the head-mounted device further includes an accelerometer; and the instructions are further configured to cause the head-mounted device to: determine that a speed of the head-mounted device exceeded a speed threshold; and based on the speed of the head-mounted device exceeding the speed threshold, output an instruction for the user to slow a performance of the exercise.

In some aspects, the techniques described herein relate to a head-mounted device, wherein the landmark includes a portion of a surface on which the user is performing the exercise.

In some aspects, the techniques described herein relate to a non-transitory computer-readable storage medium including instructions stored thereon that, when executed by at least one processor, are configured to cause a head-mounted device to: determine that a first orientation of the head-mounted device is outside a proper form range, the proper form range being based on a distance of the head-mounted device from a landmark; based on the determination that the first orientation of the head-mounted device is outside the proper form range, output an instruction for a user to correct a body posture of the user, the head-mounted device being mounted on a head of the user; determine that a second orientation of the head-mounted device is within the proper form range; determine, based on data received from a depth-sensing device and after the determination that the second orientation of the head-mounted device is within the proper form range, that a distance of the head-mounted device from a landmark is within a completion range; and based on the distance of the head-mounted device from the landmark being within the completion range, increment a repetition counter.

In some aspects, the techniques described herein relate to a non-transitory computer-readable storage medium, wherein the instructions are further configured to cause the head-mounted device to, based on the distance of the head-mounted device from the landmark being within the completion range, output an indication that a repetition has been completed.

In some aspects, the techniques described herein relate to a non-transitory computer-readable storage medium, wherein the instructions are further configured to cause the head-mounted device to, based on the determination that the second orientation of the head-mounted device is within the proper form range, output an indication that the user is performing an exercise with proper form.

In some aspects, the techniques described herein relate to a non-transitory computer-readable storage medium, wherein the completion range is based on a height of the user.

In some aspects, the techniques described herein relate to a non-transitory computer-readable storage medium wherein the landmark includes a portion of a surface on which the user is performing an exercise.

The details of one or more implementations are set forth in the accompanying drawings and the description below. Other features will be apparent from the description and drawings, and from the claims.

BRIEF DESCRIPTION OF THE DRAWINGS

Like reference symbols in the various drawings indicate like elements.

DETAILED DESCRIPTION

A head-mounted device can monitor a user performing exercises, such as push-ups, crunches, or squats. The head-mounted device can, for example, track repetitions performed by the user based on a distance of the head-mounted device from a landmark. The landmark can include a portion of a surface, such as a floor or ground that the user is performing the exercise on. The head-mounted device can, for example, consider the user to be in a starting position when the distance of the head-mounted device from the landmark is within a starting position range, and consider the user to have completed a first portion of a repetition when the distance of the head-mounted device from the landmark is within a completion range. The head-mounted device can measure the distance from the landmark based on one or more cameras included in the head-mounted device, and/or based on the one or more cameras and a gyroscope included in the head-mounted device. As used herein, "camera" can refer to depth sensors and/or range sensors such as cameras, time-of-flight (ToF) sensors, light detection and/or ranging (LiDAR) cameras.

The head-mounted device can also monitor a form of the user while the user is performing the exercise. The head-mounted device can monitor the form based on an orientation of the head-mounted device as measured by a gyroscope and/or accelerometer included in the head-mounted device. The head-mounted device can determine whether the user's form is appropriate based on whether the orientation of the head-mounted device is within an orientation range. The orientation range can change as the user proceeds through a repetition, based on the distance of the head-mounted device from the landmark.

Figure 1A:
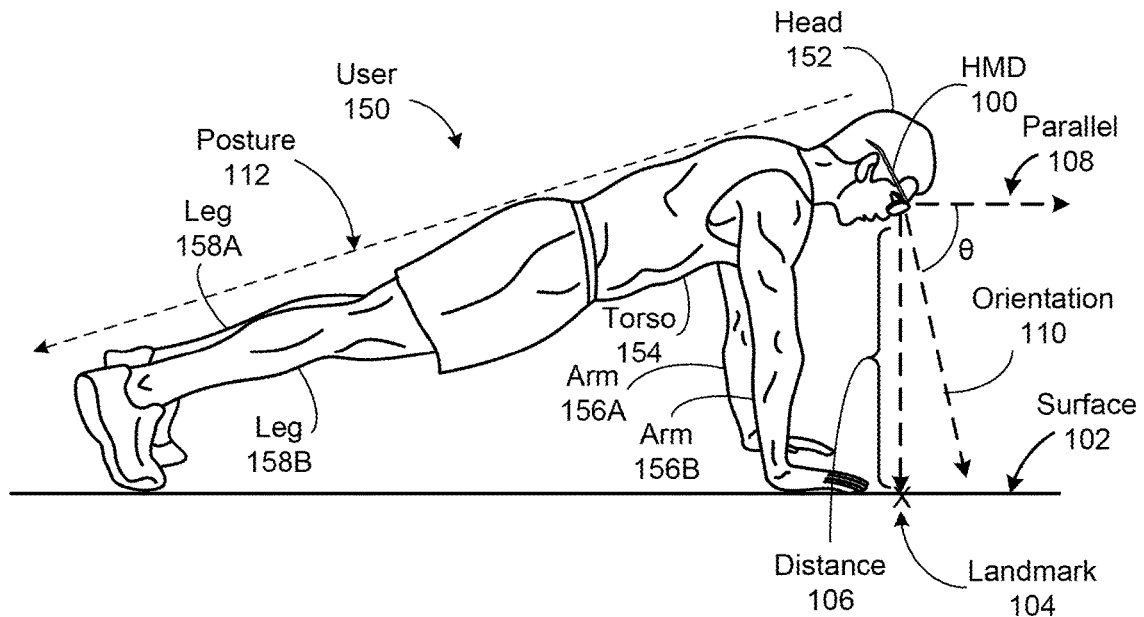
FIG. 1A shows a user performing a push-up in a starting position wearing a head-mounted device.

FIG. 1A shows a user 150 performing a push-up in a starting position wearing a head-mounted device (HMD) 100. The user 150 can place portions of the user's 150 arms 156A, 156B (such as the user's 150 hands) and legs 158A, 158B (such as the user's 150 feet) on the surface 102. The surface 102 can include a floor, ground, or other surface that the user 150 is exercising on. When the user 150 is demonstrating proper form, the user's 150 torso 154 can be straight along a posture line 112 and/or plane.

A head-mounted device 100 can be mounted on, and/or disposed on, a head 152 of the user 150. The head-mounted device 100 can include smartglasses. The head-mounted device 100 can point in a direction away from the user's 150 head 152 and/or face. The direction that the head-mounted device 100 is pointing can be considered an orientation 110 of the head-mounted device 100. The head-mounted device 100 can include an orientation sensor that can include a gyroscope and/or an accelerometer that measures the orientation 110. In some examples, the gyroscope can be included in an inertial measurement unit (IMU) that is included in the head-mounted device 100. The head-mounted device 100 and/or gyroscope can compare the orientation 110 to a parallel plane 108. The parallel plane 108 can be parallel to the surface 102. An angle Θ can measure and/or represent the difference between the orientation 110 in the parallel plane 108.

The head-mounted device 100 can measure a distance 106 between the head-mounted device 100 and a landmark 104. As used herein, the distance 106 can refer to any distance between the head-mounted device 100 and the landmark 104, and can include different distances 106A, 106B, 106C shown in FIGS. 1A, 1B, and 1C respectively. The head-mounted device 100 can measure a first distance 106A between the head-mounted device 100 and the landmark 104 when the user 150 is in the starting position of the push-up. The landmark 104 can include a portion of the surface 102. The head-mounted device 100 can select the landmark 104, and measure the distance 106A from the same landmark 104 throughout the exercise (in the example of FIG. 1A, the exercise is push-ups). The landmark 104 can be a fixed object that does not move, and/or a portion of a fixed object that does not move, to provide consistency in measuring the distance 106. The head-mounted device 100 can select the landmark 104 as an object that will remain within a field of view of a camera included in the head-mounted device 100 throughout the exercise (and/or repetitions). The landmark 104 can be within reach of the user. The head-mounted device 100 can measure the distance 106A based on one or more images of the landmark 104 captured by a camera included in the head-mounted device 100. The head-mounted device 100 can, for example, measure the distance 106A by triangulation between multiple images of the landmark 104 captured by the camera, and/or based on one or more measurements of the orientation by the gyroscope.

In the example shown in FIG. 1A, the distance 106A can be within a starting position range. The starting position range can be a function of the height of the user 150, such as a range around an estimated arm length of the user 150. A length of the user's 150 arms 156A, 156B can be estimated to be 40% of a height of the user 150, for example. In the example in which the length of the user's 150 arms 156A, 156B can be estimated to be 40% of a height of the user 150, the starting position range can be between 30% and 40% of the height of the user 150. In some examples, based on the distance 106A being within the starting position range, the head-mounted device 100 can output an instruction for the user 150 begin the exercise and/or a repetition, such as an audible output, "Down!"

In the example shown in FIG. 1A, the orientation 110 can be within a starting orientation range. In the example of a push-up, the starting orientation range for the angle Θ, measuring the difference between the orientation 110 and the parallel plane 108, can be near 90° or normal to the surface 102, such as between 80° and 90°. In this example, because the angle Θ is within the starting orientation range, the user 150 can be considered to be in the proper position to begin push-ups. Based on the orientation 110 of the head-mounted device 100 being within the starting orientation range, the head-mounted device 100 can output an instruction for the user to begin an exercise, such as push-ups. In some examples, the instruction and be an audible output such as "Begin!," or "Down!"

Figure 1B:
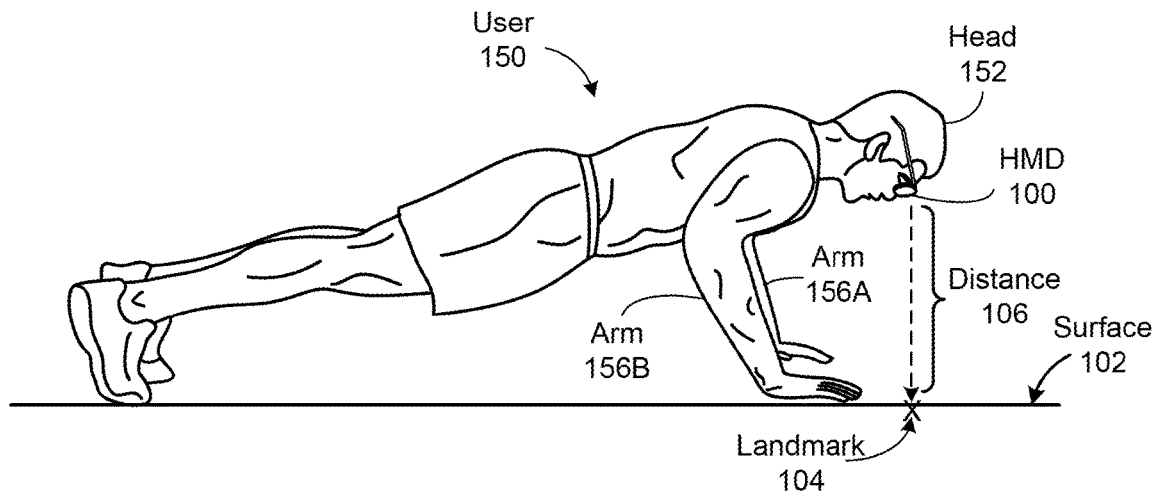
FIG. 1B shows the user performing the push-up in an intermediate position.

FIG. 1B shows the user 150 performing the push-up in an intermediate position. In this example, the user 150 has bent the user's 150 arms, and the distance 106, represented as second the distance 106B, has been reduced from the first distance 106A shown in the starting position of FIG. 1A. However, the distance 106B is still outside a completion range from the landmark 104. The completion range can also be a function of the height of the user 150. In some examples, the final position could be considered a position in which the user's head and/or the head-mounted device 100 is within 10% of the user's 150 height from the landmark 104. In the example in which the final position is considered a position in which the user's head and/or the head-mounted device 100 is within 10% of the user's 150 height from the landmark 104, the completion range can be around 10% of the user's 150 height, such as between 5% and 15% of the user's 150 height. In some examples, based on the distance 106B being outside the completion range, the head-mounted device 100 can output an instruction for the user 150 continue the exercise, such as an audible output, "Keep going!"

Figure 1C:
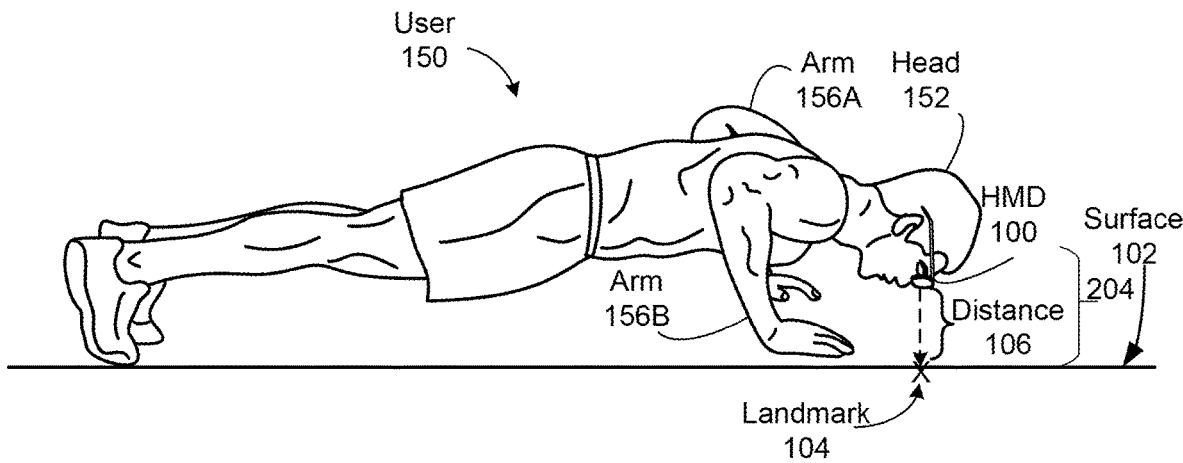
FIG. 1C shows the user performing the push-up in a bottom completed position.

FIG. 1C shows the user 150 performing the push-up in a bottom, or completed position. In this example, the user 150 has completed a first portion of the exercise, in this example, going down for a push-up. Based on completing the first portion of the exercise, the distance 106 has been reduced, and the third distance 106C is within the completion range. As shown in FIG. 1C, the third distance 106C is less than a completion distance 204. Based on the third distance 106C being less than the completion distance 204, the head-mounted device 100 can determine that the distance 106C is within a completion range 205 (shown in FIG. 2). In some examples, the head-mounted device 100 can consider the user 150 to have completed a repetition of the exercise and increment a repetition counter. In some examples, the head-mounted device 100 will consider the user 150 to have completed the repetition of the exercise only after the user 150 has returned to the starting position shown in FIG. 1A, and/or the distance 106 has returned to the starting position range.

Figure 1D:
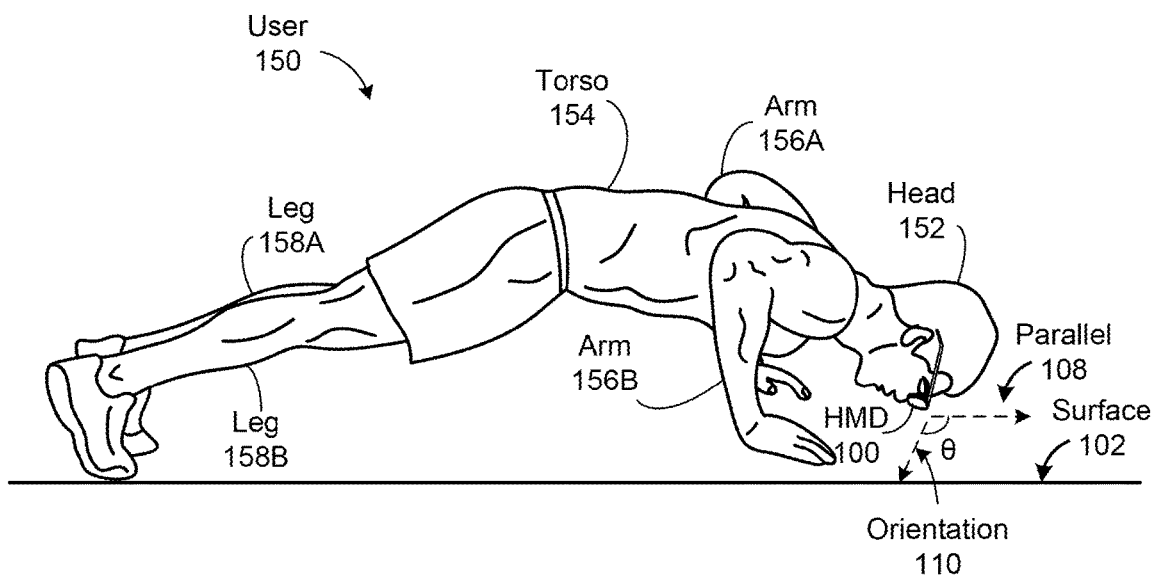
FIG. 1D shows the user performing the push-up in a form in which the user's hips are too high.

FIG. 1D shows the user 150 performing the push-up in a form in which the user's 150 hips are too high. With the user's 150 hips too high, an angle Φ will be less than 180°, and the user's 150 head 152 will sink down, causing the angle Θ, which represents the difference between the orientation 110 and the parallel plane 108, to be outside an orientation range and/or greater than 90°. Based on the angle Θ being outside the orientation range and/or greater than 90°, the head-mounted device 100 can output an indication that the form of the user 150 is incorrect. In some examples, the indication could be an audible output, such as, "Lower your hips."

Figure 1E:
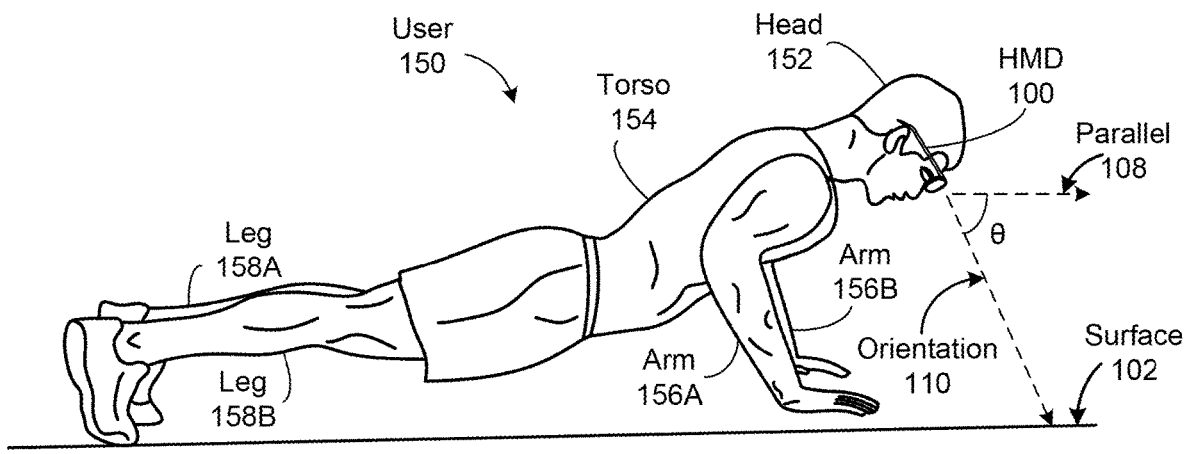
FIG. 1E shows the user performing the push-up in a form in which the user's hips are too low.

FIG. 1E shows the user 150 performing the push-up in a form in which the user's 150 hips are too low. With the user's 150 hips too low, the angle Φ will be greater than 180°, and the user's 150 head 152 will lift up, causing the angle Θ, which represents the difference between the orientation 110 and the parallel plane 108, to be outside an orientation range and/or less than a threshold form value such as 80°. Based on the angle Θ being outside the orientation range and/or less than the threshold form value (such as) 80°, the head-mounted device 100 can output an indication that the form of the user 150 is incorrect. In some examples, the indication could be an audible output, such as, "Lift your hips."

Figure 2:
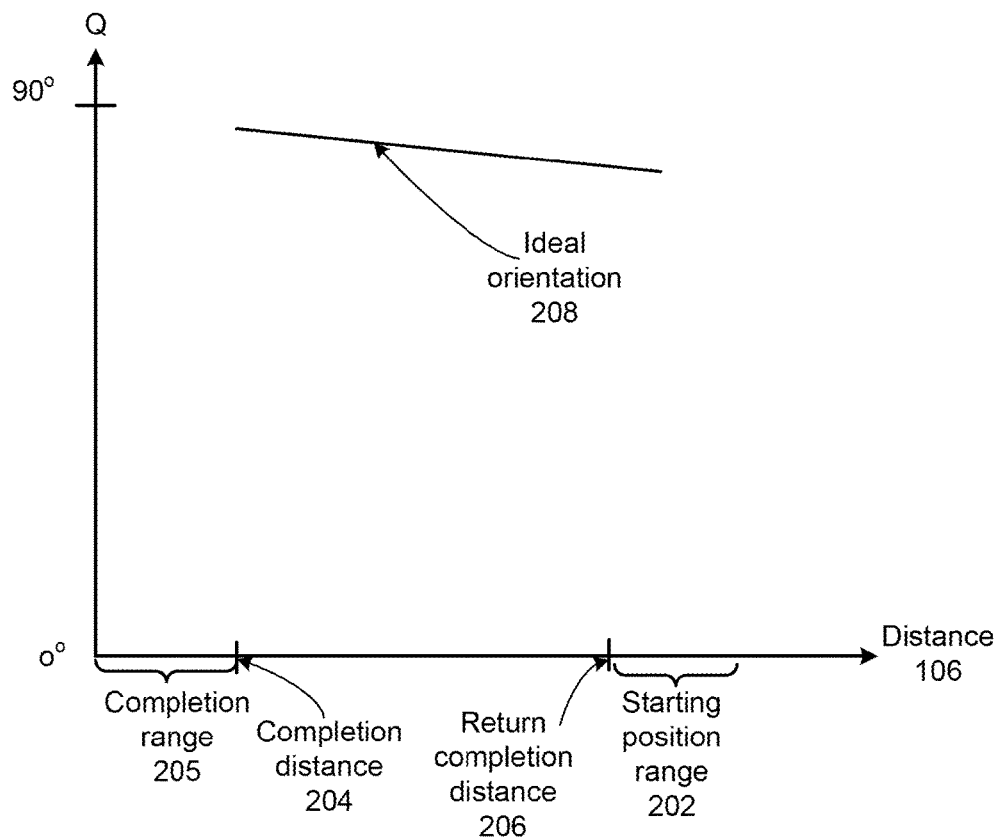
FIG. 2 shows a graph with distance thresholds and ideal orientation as a function of distance.

FIG. 2 shows a graph with distance thresholds and ideal orientation as a function of distance. The starting position range 202 can include distances in which the distance 106 is greater than or equal to a return completion distance 206. A completion range 205 can include distances in which the distance 106 is less than or equal to a completion distance 204. The completion range 205 can represent a range of distances 106 within which the user 150 can be considered to have completed a first portion of the exercise.

The completion distance 204 can represent, for example a distance 106 of the head-mounted device 100 from the surface 102 and/or landmark 104 when the user 150 has completed a first portion, and/or half of, a repetition of an exercise. The completion distance 204 and/or completion range 205 can be a distance or location at which the user stops and/or changes direction of movement during the exercise. In the examples of push-ups and squats, the completion distance 204 can represent the distance 106 when the user 150 has reached the bottom of the exercise, as shown in FIG. 1C in the example of push-ups. In the example of crunches, the completion distance 204 can represent the distance 106 when the user 150 has reached the top of the exercise. The completion range 205 can represent any value lower than the completion distance 204, to take into account situations in which the user 150 moves beyond the completion distance 204.

The return completion distance 206 can represent a distance 106 when the user 150 has returned to the starting position of the exercise, such as with the user's 150 arms 156A, 156B fully extended when doing push-ups, as shown in FIG. 1A, or in a standing position doing squats. The return completion distance 206 and/or starting position range 202 can be a distance or location at which the user stops and/or changes direction of movement during the exercise after having completed a repetition of the exercise. The starting position range 202 can include any value for the distance 106 that is greater than the return completion distance 206, and allows the return completion distance 206 to have a value that is less than the distance 106A when the user 150 is fully extended, allowing for some tolerance in the user's 150 movements.

The head-mounted device 100 can determine the completion distance 204, completion range 205, return completion distance 206, and/or starting position range 202 as functions of a height of the user 150. In some examples, the return completion distance 206 can be, for example, 40% of the height of the user 150, and the starting position range 202 can be any value that is equal to or greater than the return completion distance 206. In some examples, the completion distance 204 can be half the return completion distance 206, or the completion distance 204 can be 10% of the height of the user 150. In some examples, the completion range 205 can be any value that is less than or equal to the completion distance 204.

In some examples, the return completion distance 206 and completion distance 204 can be functions of the distance 106A the head-mounted device 100 when the user 150 is in a starting or plank position with the arms 156A, 156B of the user 150 straight, as shown in FIG. 1A. In some examples, the head-mounted device 100 can determine the distance 106A while the user 150 is in the starting position, and thereafter determine the return completion distance 206 and the completion distance 204 as functions of the distance 106A while the user 150 is in the starting position. In some examples, the return completion distance 206 can be 60% of the distance 106A when the user 150 is in the starting position, and/or the completion distance 204 can be 10% of the distance 106A when the user 150 is in the starting position.

The ideal orientation 208 can be a function of the distance 106. For example, when the user 150 has completed the push-up as shown in FIG. 1C, and the distance 106 is at or near the completion distance 204, and/or the distance 106 is within the completion range, the ideal orientation 208, and/or ideal value of Θ, can be 90°. When the user 150 is in the starting position shown in FIG. 1A, the ideal orientation 208 can be a value less than 90°, such as 80°. In some examples, the angle of the ideal orientation 208 can be an inverse cosine of the distance 106 divided by the height of the user 150. The orientation range, or range around the ideal orientation 208, can be the ideal orientation 208 plus or minus a specified number of degrees, such as plus or minus 2° or plus or minus 3°.

Figure 3:
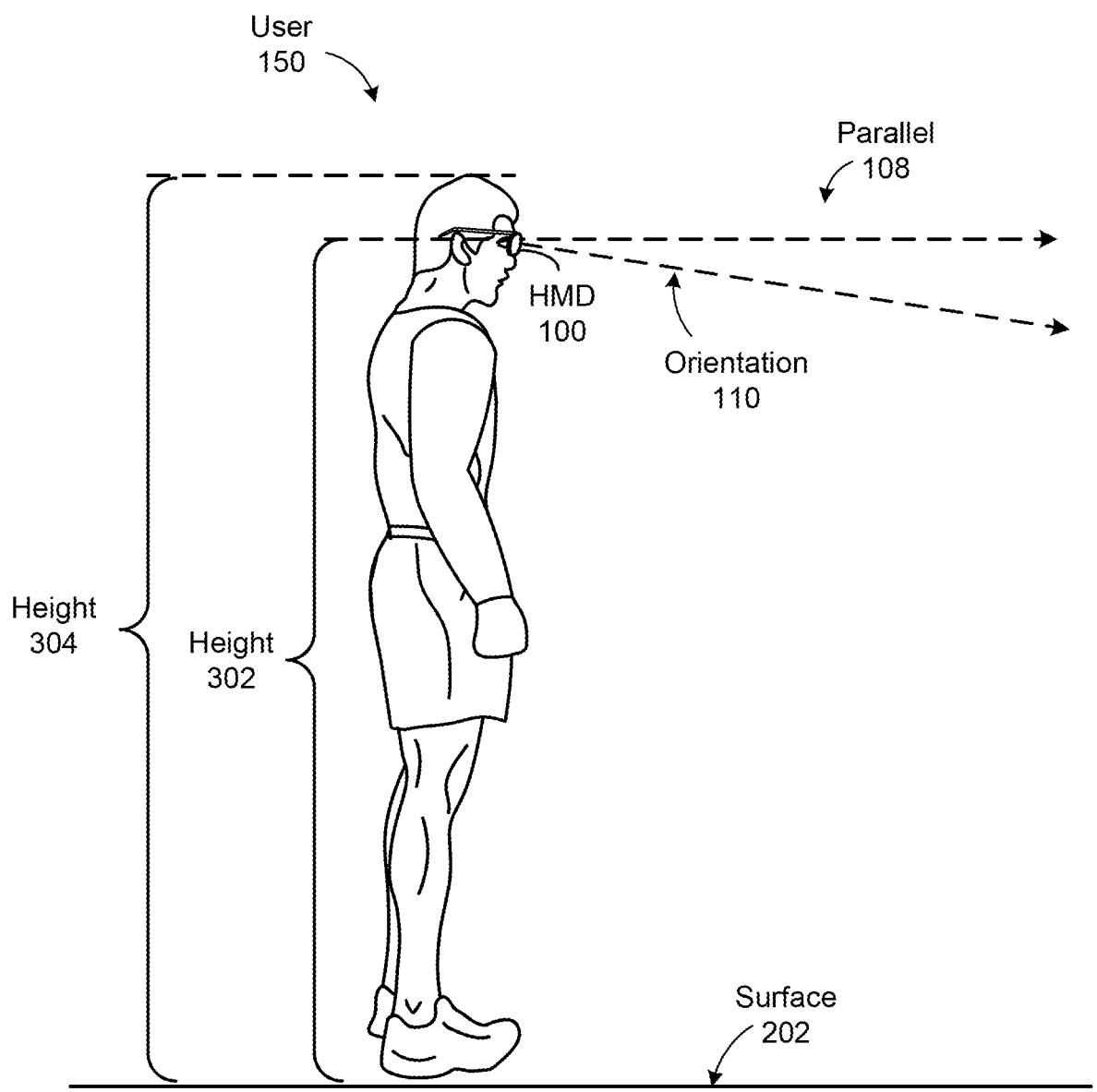
FIG. 3 shows height measurements of the user in a standing position wearing the head-mounted device.

FIG. 3 shows height measurements of the user 150 in a standing position wearing the head-mounted device 100. In some examples, the head-mounted device 100 can determine a height of the user 150 while the user 150 is in a standing position.

In the example shown in FIG. 3, the user 150 is standing on the surface 102. The user 150 can look around, enabling the head-mounted device 100 to capture one or multiple images via a camera included in the head-mounted device 100. The movement by the user 150 can also cause the head-mounted device 100 to move to different orientations 110. FIG. 3 shows the angle Θ between the orientation 110 in the parallel plane 108, which is parallel to the surface 102.

Based on capturing one or multiple images, and/or the multiple orientations 110, the head-mounted device 100 can determine either a height 302 from the head-mounted device 100 to the surface 102, or a height 304 from a top of the user's 150 head to the surface 102. The head-mounted device 100 can use either height 302, 304 to determine the completion distance 204, completion range, return completion distance 206, and/or starting position range 202. In some examples, the head-mounted device 100 can determine the user's 150 height 304 based on user input, such as the user 150 orally stating the user's 150 height, or the user 150 manually inputting the user's 150 height 304 into the head-mounted device 100 or another device in communication with the head-mounted device 100.

Figure 4:
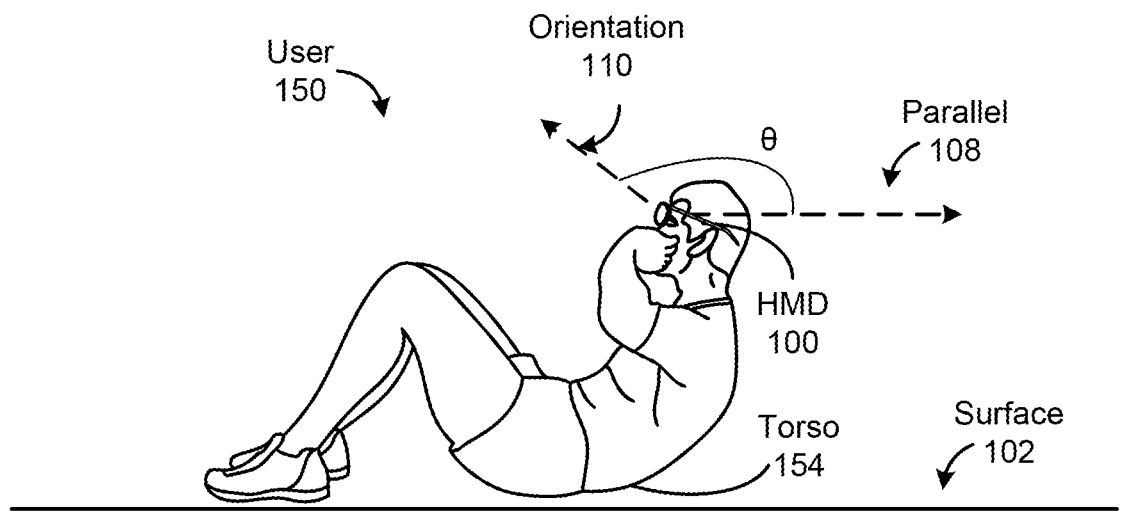
FIG. 4 shows the user performing a crunch wearing the head-mounted device.

FIG. 4 shows a user 150 performing a crunch wearing the head-mounted device 100. A crunch, which can also be referred to as a "situp," is another example of an exercise that the head-mounted device 100 can monitor the user 150 performing and track repetitions. In the example of a crunch, a first portion of the exercise will include the user 150 raising the user's 150 head and/or torso 154 away from the surface 102, and thereby increasing the distance of the user's 150 head and/or torso 154 from the surface 102. In the example of the crunch, the second portion of the exercise can include the user 150 lowering the user's 150 head and/or torso 154 back toward the surface 102, and thereby decreasing the distance of the user's 150 head and/or torso 154 from the surface 102. The head-mounted device 100 can rely on a portion of the surface 102 as a landmark, or select another object within a field of view in front of the user's 150 head.

In some examples, the head-mounted device 100 can track the user's 150 movement and/or progress through the crunch exercise based on the orientation 110 of the head-mounted device 100. The orientation 110 of the head-mounted device 100 can be measured by the angle Θ, which measures the difference between the angle of the orientation 110 of the head-mounted device 100 and the parallel plane 108, which is parallel to the surface 102.

Figure 5:
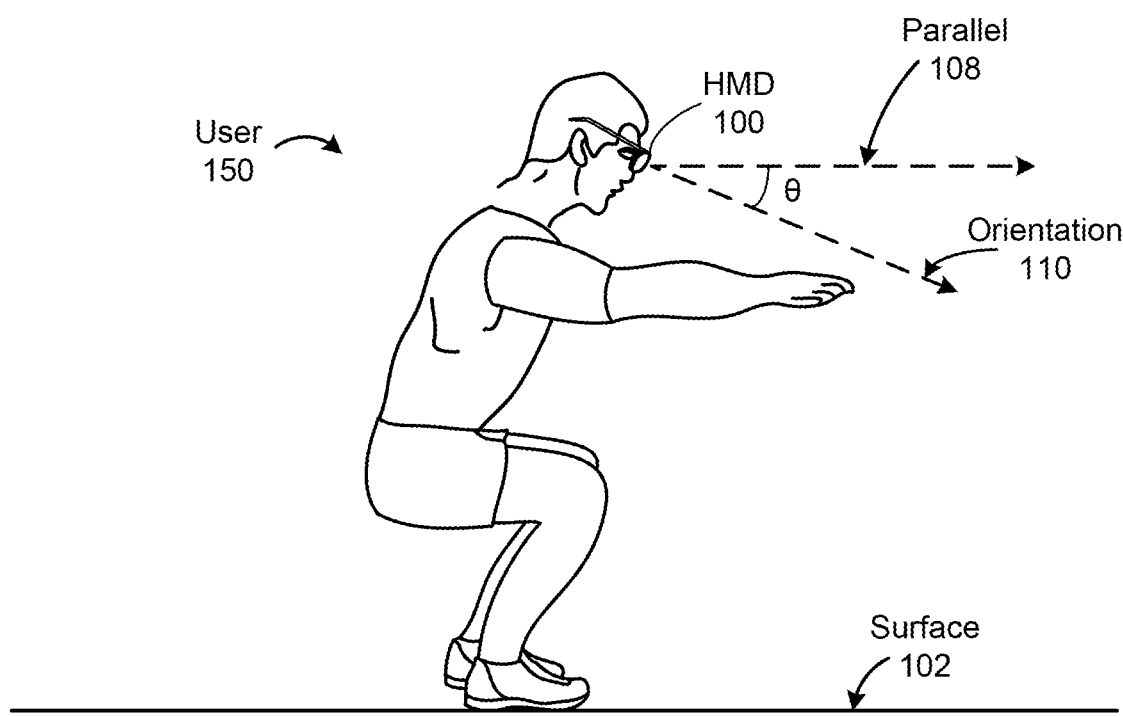
FIG. 5 shows the user performing a squat wearing the head-mounted device.

FIG. 5 shows the user 150 performing a squat wearing the head-mounted device 100. In the example of the user 150 performing the squat as an exercise, the user 150 can bend the user's 150 legs to move down in a first portion of the exercise, and straighten the user's 150 legs to move up in a second portion of the exercise. The head-mounted device 100 can monitor the form of the user 150 performing the squat based on the orientation 110 of the head-mounted device 100. In this exercise, proper form can dictate that the angle Θ, which measures the difference between the orientation 110 of the head-mounted device 100 and the parallel plane 108, be near zero, such as within a threshold range of zero such as within 10° of zero.

In the example of the squat, the return completion distance 206 can be the user's 150 height, and/or near the user's 150 height, such as 90% of the user's 150 height, and/or the starting position range 202 can be a value equal to or greater than 90% of the user's 150 height. In some examples, the completion distance 204 can be 70% of the user's 150 height, and/or the completion range can be less than or equal to 70% of the user's 150 height, requiring the user to squat down 30% of the user's 150 height.

Figure 6:
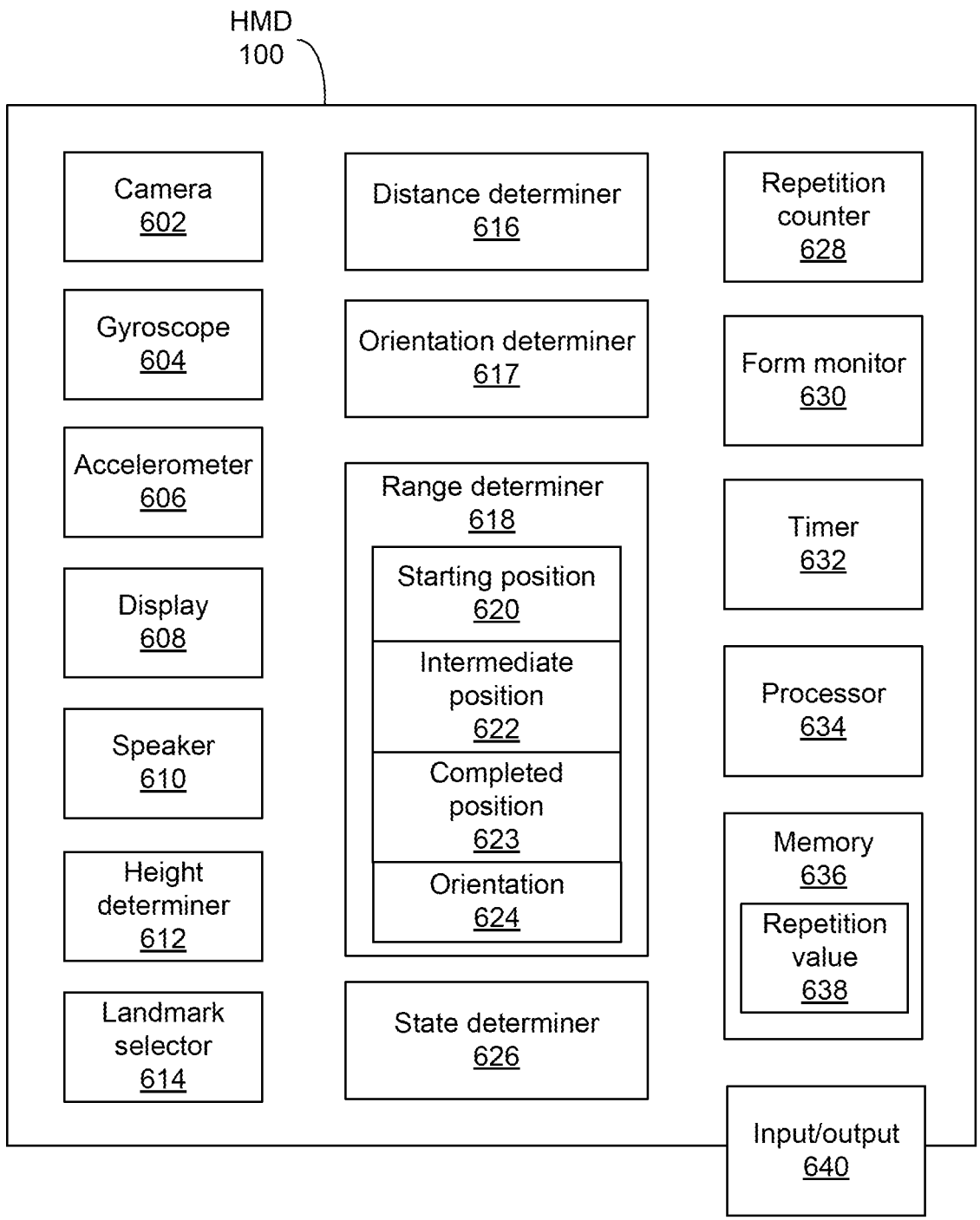
FIG. 6 is a block diagram of the head-mounted device.

FIG. 6 is a block diagram of the head-mounted device 100. The head-mounted device 100 can include any combination of modules described herein.

The head-mounted device 100 can include a camera 602. The camera 602 can include one or more cameras, such as one or more cameras that capture images from the same direction that the user's 150 eyes capture images, and/or one or more gaze-tracking cameras, which capture images of the user's 150 eyes for purposes of tracking the user's 150 eyes. The camera 602 can capture images, such as images of the landmark 104 and/or other objects. The camera 602 can include a camera that captures light, and/or one or more depth sensors and/or range sensors such as cameras, time-of-flight (ToF) sensors, light detection and/or ranging (LiDAR) cameras. The camera 602 and/or depth sensing device can capture image data and/or data based on which the head-mounted device 100 can determine distances 106, such as distances 106 from the landmark 104.

The head-mounted device 100 can include a gyroscope 604. The gyroscope 604 can determine the orientation 110 of the head-mounted device 100. The gyroscope 604 can determine the orientation 110 of the head-mounted device with respect to the parallel plane 108 that is parallel to the surface 102 of the earth, and/or with respect to a direction that is normal to the surface 102 of the earth and/or extends through the center of the earth.

The head-mounted device 100 can include an accelerometer 606. The accelerometer 606 can measure acceleration, velocity, and/or movement of the head-mounted device 100. In some examples, the gyroscope 604 and accelerometer 606 can be included in an inertial measurement unit (IMU) that is included in the head-mounted device.

In some examples, the head-mounted device 100 can use the accelerometer 606, and/or the accelerometer 606 and the camera 602, to determine that a speed of the head-mounted device 100, which can indicate a speed at which the user 150 is performing the exercise. The head-mounted device 100 can determine whether the speed exceeds a speed threshold, which could indicate that the user 150 is at risk of injuring the user's 150 joints during the exercise. If the speed is exceeding the speed threshold, the head-mounted device 100 can, based on the speed of the head-mounted device 100 exceeding the speed threshold, output an instruction for the user 150 to slow a performance of the exercise. The speaker 610 could, for example, output an audible instruction, "Slow down."

The head-mounted device 100 can include a display 608. The display 608 can present graphical output to the user 150. The display 608 can be included on an inner portion of the head-mounted device 100, facing the user's 150 eyes. In some examples, the display 608 can include a graphical representation of a current body position of the user 150, such as a representation of the form of the user 150 performing the exercise, and/or an indication of whether the user is performing the exercise with proper form (such as whether the hips of the user 150 are too low or too high in the example of push-ups or whether the back of the user is leaning too far forward in the example of squats). In some examples, the display 608 can also indicate the number of repetitions that the user has performed. In some examples, color presented by the display 608 could indicate whether the form of the user 150 is proper, such as green indicating proper form and red indicating improper form.

The head-mounted device can include a speaker 610. The speaker 610 can include one or more speakers that provide audible output to the user 150.

The head-mounted device can include a height determiner 612. The height determiner 612 can determine a height 302, 304 of the user 150. In some examples, the height determiner 612 can determine the height 302, which can be a distance from the head-mounted device 100 to a closest portion of the surface 102, based on triangulating multiple images captured by the camera 602, and/or based on angles and/or orientation data measured by the gyroscope 604. The height determiner 612 can determine the height 302, 304 using techniques described with respect to a distance determiner 616.

The head-mounted device 100 can include a landmark selector 614. The landmark selector 614 can select the landmark 104, which will be an object and/or location that serves as a reference point for the head-mounted device 100 to determine the distance 106. In some examples, the landmark selector 614 can select a landmark 104 that is a closest portion of the surface 102 from the head-mounted device 100. In some examples, the landmark selector 614 can select a landmark 104 that has features that make recognition errors unlikely.

The head-mounted device 100 can include a distance determiner 616. The distance determiner 616 can determine the distance 106 of the head-mounted device 100 from the landmark 104. The distance determiner 616 can determine the distance 106 based on images captured by the camera 602 and/or angles measured by the gyroscope 604. The distance determiner 616 can determine the distance 106 by a monocular vision method, a log mapping method, or method of regression coefficient analysis using data extracted from captured photos, with a single camera 602, or self localization using a single camera 602 and the varying orientation 110 of the head-mounted device 100, as non-limiting examples. In some examples, the distance determiner 616 can determine distances based on image data captured by the camera 602 and/or orientation data received from the gyroscope 604.

The head-mounted device 100 can include an orientation determiner 617. The orientation determiner 617 can determine the orientation 110 of the head-mounted device 100. In some examples, the orientation determiner 617 also determines the angle Θ, which measures the difference between the orientation 110 in the parallel plane 108. The orientation determiner 617 can determine the orientation of the head-mounted device 100 based on orientation data received from the gyroscope 604.

The head-mounted device 100 can include a range determiner 618. The range determiner 618 can determine ranges, such as a starting position range, an intermediate position range, a completion range, and/or orientation ranges. The ranges that are based on distance can be based on the determined height 302, 304 of the user 150. The ranges can also depend on a category of the exercise. For example, the ranges can be different for the category of push-ups, the category of crunches, and/or the category of squats.

The range determiner 618 can include a starting position range determiner 620. The starting position range determiner 620 can determine the starting position range 202 shown in FIG. 2. The starting position range determiner 620 can determine the starting position range 202 based on the category of exercise. In the example of push-ups, the starting position range determiner 620 can determine the starting position range 202 as, for example, between 30% and 40% of the height 302, 304 of the user 150. In the example of crunches, the starting position range determiner 620 can determine the starting position range 202 as a small distance from the surface 102 such as for example, 10% of the height 302, 304 of the user 150 from the surface 102. In the example of squats, the starting position range determiner 620 can determine the starting position range 202 as being at least 90% of the height 302, 304 of the user 150 from the surface 102. For certain exercises, such as push-ups and squats, the starting position range determiner 620 can determine the starting position range 202 as a minimum distance, such as at least 30% of the height 302, 304 of the user 150 for push-ups and at least 90% of the height 302, 304 of the user 150 for squats. For certain exercises, such as crunches, the starting position range determiner 620 can determine the starting position range 202 as a maximum distance 106 from the surface 102, such as a maximum of and/or no more than 10% of the height 302, 304, from the surface 102.

The range determiner 618 can include an intermediate position range determiner 622. The intermediate position range determiner 622 can determine a range within which the user is not considered to be either in the starting position or the complete position. The intermediate position range determined by the intermediate position range determiner 622 can include, for example, distances 106 that are outside the starting position range 202 and are outside the completion distance range, and/or are between the return completion distance 206 and the completion distance 204. The intermediate position range determiner 622 can determine the intermediate position range based on the category of exercise.

The range determiner 618 can include a completed position range determiner 623. The completed position range determiner 623 can determine a completion range 205, which can be considered a range for the distance 106 within which the user 150 can be considered to have completed a first portion of the exercise. The completed position range determiner 623 can determine the completion range 205 based on the category of exercise.

In some examples, the completed position range determiner 623 can determine the completion range 205 as a ratio of the height 302, 304 of the user 150. For example, when the exercise is push-ups, the completed position range determiner 623 can determine that the completion distance 204 is 10% of the height 302, 304 of the user 150, or less than or equal to 50% of the return completion distance 206. When the exercise is squats, the completed position range determiner 623 can determine that the completion distance 204 is 70% of the height 302, 304 of the user 150. When the exercise is crunches, the completed position range determiner 623 can determine that the completion distance 204 is 20% of the height 302, 304 of the user 150 from the surface 102.

In some examples, the completed position range determiner 623 can change the completion distance 204 to modify the difficulty of the exercise. For example, the completed position range determiner 623 could reduce the completion distance 204 to make push-ups and/or squats more difficult. The completed position range determiner 623 could change the completion distance 204, such as by reducing the completion distance 204 based on an exercise history of the user 150, which could include a current exercise session and/or previous exercise sessions. In some examples, if the user 150 had previously completed a given number of repetitions of an exercise, the completed position range determiner 623 could make the exercise more difficult by changing the completion distance 204 such as by reducing the completion distance 204. In some examples, the completed position range determiner 623 could make the exercise more difficult by changing the completion distance 204 such as by reducing the completion distance 204 of the user 150 was completing repetitions quickly during an exercise session, which can be considered an indication that the completion distance 204 was too easy for the user 150.

The range determiner 618 can include an orientation range determiner 624. In some examples, the orientation range determiner 624 can determine a range for the orientation 110 and/or Θ within which the user 150 can be considered to be performing an exercise with proper form. The orientation range determiner 624 can determine the range based on a category of the exercise. The orientation range determined by the orientation range determiner 624 can be a band and/or range around the ideal orientation 208 shown in FIG. 2.

In the example of push-ups, the angle of the ideal orientation 208 can be an inverse cosine of the distance 106 divided by the height of the user 150. The orientation range, or range around the ideal orientation 208, such as the ideal orientation 208 plus or minus a specified number of degrees, such as plus or minus 2° or plus or minus 3°.

In the example of squats, the angle of the ideal orientation 208 can be zero, and the orientation range can be plus or minus a specified number of degrees, such as plus or minus 2° or plus or minus 3°.

In the example of crunches, the angle of the ideal orientation 208 can be an inverse cosine of the distance 106 divided by half of the height of the user 150 (because only the torso 154 of the user 150 is moving). The orientation range, or range around the ideal orientation 208, such as the ideal orientation 208 plus or minus a specified number of degrees, such as plus or minus 2° or plus or minus 3°.

The head-mounted device 100 can include a state determiner 626. The state determiner 626 can determine a state of the user 150 within an exercise. The state determiner 626 can determine, for example, whether the user 150 is in a starting position, an intermediate position, or a completed position. For example, the state determiner 626 can determine that the user 150 is in the starting position based on the distance 106 determined by the distance determiner 616 being within the starting position range 202. The state determiner 626 can determine that the user 150 is in an intermediate position based on the distance 106 determined by the distance determiner 616 being within an intermediate range, and/or between the starting position range and the completed position range. The state determiner 626 can determine that the user is in the completed position based on the distance 106 determined by the distance determiner 616 being within the completion range 205.

The head-mounted device 100 can include a repetition counter 628. The repetition counter 628 can increment a repetition value when the user 150 completes a repetition, and/or when the user 150 completes a portion of the exercise. In some examples, the repetition counter 628 can increment the repetition value when the state determiner 626 determines that the user 150 has entered the completion range 205. In some examples, the repetition counter 628 can increment a repetition value when the state determiner 626 determines that the user 150 has entered the completion range 205 and then returned to the starting position range 202. In some examples, the speaker 610 can output an audible notification to the user 150 when the repetition counter 628 increments the repetition value, such as by audibly stating the number of repetitions that the user 150 has completed.

The head-mounted device can include a form monitor 630. The form monitor 630 can determine when the orientation 110, Θ of the user 150 determined by the orientation determiner 617 falls outside the orientation range determined by the orientation range determiner 624. In some examples, the speaker 610 can output an audible notification to the user 150 to correct a body posture of the user 150 when the form monitor 630 determines that the form of the user 150 has fallen outside the orientation range. For example, the speaker 610 can instruct the user 150 to, "Lower your hips," when the form monitor 630 determines that the orientation 110 of the head-mounted device 100 is too low, and/or the speaker 610 can instruct the user 150 to, "raise your hips," when the form monitor 630 determines that the orientation 110 of the head-mounted device 100 is too high.

The head-mounted device 100 can include a timer 632. The timer 632 can maintain a timer indicating how long the user 150 has maintained a position, such as a starting position or completed position. In some examples, the display 608 can indicate to the user 150 the time that the user 150 has maintained the position. The user 150 may, for example, want to maintain a specific position for a predetermined amount of time before returning to a different position.

The head-mounted device 100 can include at least one processor 634. The at least one processor 634 can execute instructions, such as instructions stored in at least one memory device 636, to cause the head-mounted device 100 to perform any combination of methods, functions, and/or techniques described herein.

The head-mounted device 100 can include at least one memory device 636. The at least one memory device 636 can include a non-transitory computer-readable storage medium. The at least one memory device 636 can store data and instructions thereon that, when executed by at least one processor, such as the processor 634, are configured to cause the head-mounted device 100 to perform any combination of methods, functions, and/or techniques described herein. Accordingly, in any of the implementations described herein (even if not explicitly noted in connection with a particular implementation), software (e.g., processing modules, stored instructions) and/or hardware (e.g., processor, memory devices, etc.) associated with, or included in, the head-mounted device 100 can be configured to perform, alone, or in combination with the head-mounted device 100, any combination of methods, functions, and/or techniques described herein.

The at least one memory device 636 can store a repetition value 638. The repetition value can start at zero when the user 150 begins an exercise. The repetition counter 628 can increment the repetition value 638 each time the user 150 completes a repetition of the exercise.

The head-mounted device 100 can include at least one input/output node 640. The at least one input/output node 640 may receive and/or send data, such as from and/or to, the head-mounted device 100 and another electronic device, and/or may receive input and provide output from and to the user 150. The input and output functions may be combined into a single node, or may be divided into separate input and output nodes. The input/output node 640 can include the camera 602, the gyroscope 604, the accelerometer 606, the display 608, the speaker 610, and/or any wired or wireless interfaces (such as Bluetooth or Institute for Electrical and Electronics Engineers 802.11) for communicating with other electronic devices.

Figure 7:
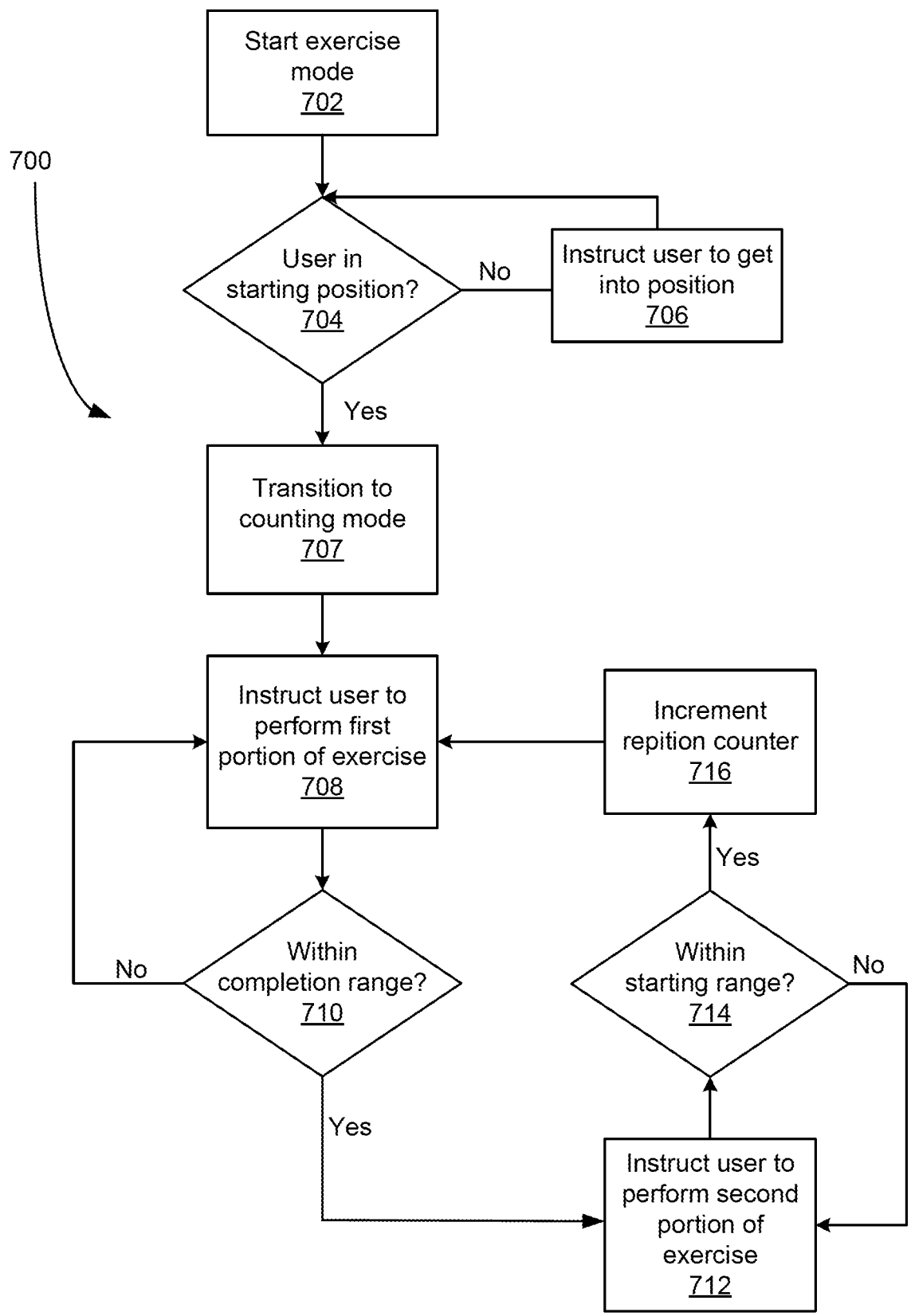
FIG. 7 is a flowchart showing a method performed by the head-mounted device.

FIG. 7 is a flowchart showing a method performed by the head-mounted device 100. The head-mounted device 100 can start an exercise mode (702), such as a push-up mode, a crunch mode, or squats mode. In some examples, the head-mounted device 100 can start the exercise mode based on user input, such as the user 150 stating, "push-ups," "crunches," or "squats," as non-limiting examples. In some examples, the head-mounted device 100 can start the exercise mode (702) based on determined movement of the head-mounted device 100 detected by the accelerometer 606 matching a pattern that is stored in association with a particular exercise (such as push-ups, crunches, or squats). In some examples, the head-mounted device 100 can start the exercise mode (702) based on changing distances 106 determined by the head-mounted device 100 matching a pattern that is stored in association with a particular exercise (such as push-ups, crunches, or squats).

After starting the exercise mode (702), the head-mounted device 100 can determine whether the user is in a starting position (704). In the example of push-ups, the head-mounted device 100 can determine whether the user is looking down and within a predetermined distance 106 of the surface 102, such as based on the orientation determiner 617 determining that the angle Θ is within a predetermined margin (such as 10°) of 90°, and/or whether the distance 106 is within the starting position range 202. In the example of squats, the head-mounted device 100 can determine whether the user is standing up and looking forward, such as whether the distance 106 is within the starting position range 202 of at least 90% of the user's 150 height 302, 304 and the orientation 110 shows that the user 150 is looking forward, such as the angle Θ being within 10° of zero (0°). In the example of crunches, the head-mounted device 100 can determine whether the distance 106 is within the starting position range 202, such as being no more than 10% of the height 302, 304 of the user 150, and the orientation 110 of the head-mounted device 100 indicating that the user 150 is looking up, such as the angle Θ being within a starting orientation range that can be considered a predetermined range of normal to the parallel plane 108, such as between 80° and 100° from parallel to the surface 102.

In some examples, the determination that the user 150 is in the starting position (704) can include a determination that the repetition of the exercise has yet to be completed (and/or has not yet been completed). In some examples, the determination that the repetition of the exercise has yet to be completed can include a determination that the distance is outside the completion range 205.

If the head-mounted device 100 determines that the user 150 is not in the starting position, then the head-mounted device 100 can instruct the user 150 to get into the starting position (706). In some examples, the head-mounted device 100 can instruct the user 150 to get into the starting position (706) by outputting an audible instruction such as, "Get into position!"

If the head-mounted device 100 determines that the user is in the starting position, then the head-mounted device 100 can transition into a counting mode (707). The counting mode can include determining whether the user 150 has completed a repetition and/or what state within the exercise the user 150 is in, and/or maintaining a count of the number of repetitions that the user 150 has completed. Transitioning to the counting mode (707) can include setting the counter to zero. In some examples, the transitioning to a counting mode in (706) can include determination that the distance 106 is outside the completion range.

After transitioning to the counting mode (707), the head-mounted device 100 can instruct the user 150 to perform a first portion of the exercise (708). In some examples, the instruction to perform the first portion of the exercise (708) can include an indication that the repetition has yet to be completed. The instruction to perform the first portion of the exercise (708) can include an audible output by the speaker 610. In the examples in which the exercise is a push-up or squat, the instruction to perform the first portion of the exercise (708) can include an audible instruction, "Down!" In the example in which the exercise is a crunch, the instruction to perform the first portion of the exercise (708) can include an audible instruction "Up!" In some examples, when the completed position range determiner 623 changed the completion distance 204 to make the exercise more difficult for the user 150, the head-mounted device 100 can instruct the user 150, such as by audible output, to continue the exercise, such as by providing audible output, "Keep going down!," in examples in which the exercise is push-ups or squats.

In some examples, before instructing the user 150 to perform the first portion of the exercise (708), the head-mounted device 100 can determine that the user 150 has left the starting position, and/or entered an intermediate position, such as by bringing the distance 106 within an instruction threshold distance of the surface 102.

After instructing the user 150 to perform the first portion of the exercise (708), the head-mounted device 100 can determine whether the distance 106 is within the completion range 205 (710). In the example of a push-up, the determination of whether the user 150 is within the completion range 205 (710) can include determining whether the user 150 has lowered the user 150 to be sufficiently close to the surface 102. If the head-mounted device 100 determines that the user 150 and/or head-mounted device 100 is not within the completion range 205, then the head-mounted device 100 will again instruct the user 150 to perform the first portion of the exercise (708).

If the head-mounted device 100 determines that the user 150 and/or head-mounted device 100 is within the completion range 205, the head-mounted device 100 can instruct the user 150 to perform a second portion of the exercise (712).

In some examples, the instruction to perform the second portion of the exercise (712) can include an indication that the repetition has been completed. The instruction to perform the second portion of the exercise (712) can include an audible output by the speaker 610. In the examples in which the exercise is a push-up or squat, the instruction to perform the first portion of the exercise (712) can include an audible instruction, "Up!" In the example in which the exercise is a crunch, the instruction to perform the first portion of the exercise (708) can include an audible instruction, "Down!"

After instructing the user 150 to perform the second portion of the exercise (712), the head-mounted device 100 can determine whether the user 150 and/or head-mounted device 100 is within the starting position range 202 (714), and/or whether the user 150 has completed the second portion of the exercise. The head-mounted device 100 can, for example, determine whether the distance 106 is within the starting position range 202. If the head-mounted device 100 determines that the user 150 and/or head-mounted device 100 is not within the starting position range 202, and/or that the second portion of the exercise has not been completed, then the head-mounted device 100 can again instruct the user 150 to perform a second portion of the exercise (712).

If the head-mounted device 100 determines that the user 150 and/or head-mounted device 100 is within the starting position range 202, and/or that the second portion of the exercise has been completed, the head-mounted device 100 can increment the repetition counter (716), adding one to the repetition value. In some examples, the head-mounted device 100 can increment the repetition counter 628 (716) after determining that the user 150 and/or head-mounted device 100 was within the completion range 205 at (710). In some examples, the head-mounted device 100 can output the repetition value 638, informing the user 150 how many repetitions the user 150 has completed, such as providing an audible output with the repetition value or the display 608 indicating a number that represents the repetition value 638. After incrementing the repetition counter (716), the head-mounted device 100 can again instruct the user 150 to perform the first portion of the exercise (708). In some examples, if the user 150 had a goal of how many repetitions of the exercise to complete, the head-mounted device 100 could compare the repetition value 638 to the goal, and if the repetition value 638 met and/or was equal to the goal, the head-mounted device 100 could inform the user 150 that the user 150 had met the goal instead of instructing the user 150 to perform the first portion of the exercise (708).

In some examples, at any time while the head-mounted device 100 is performing the method, the form monitor 630 can determine whether the orientation 110 is within the proper form range, which can also be considered an orientation range. If the form monitor 630 determines that the orientation 110 is outside the proper form range, then the form monitor 630 can instruct a module in the head-mounted device 100, such as the speaker 610, to output instruction to the user 150 to correct a body posture. The form monitor 630 can continue causing the instruction to the user 150 to correct a body posture until the form monitor 630 determines that the orientation 110 is within the proper form range and/or orientation range. In some examples, at any time while the head-mounted device 100 is performing the method 700, the display 608 can provide visual feedback to the user 150 regarding the form of the user 150 performing the exercise, such as a graphical indication of the form of the user 150 and/or and indication of whether the form is the user is proper or improper.

Figure 8:
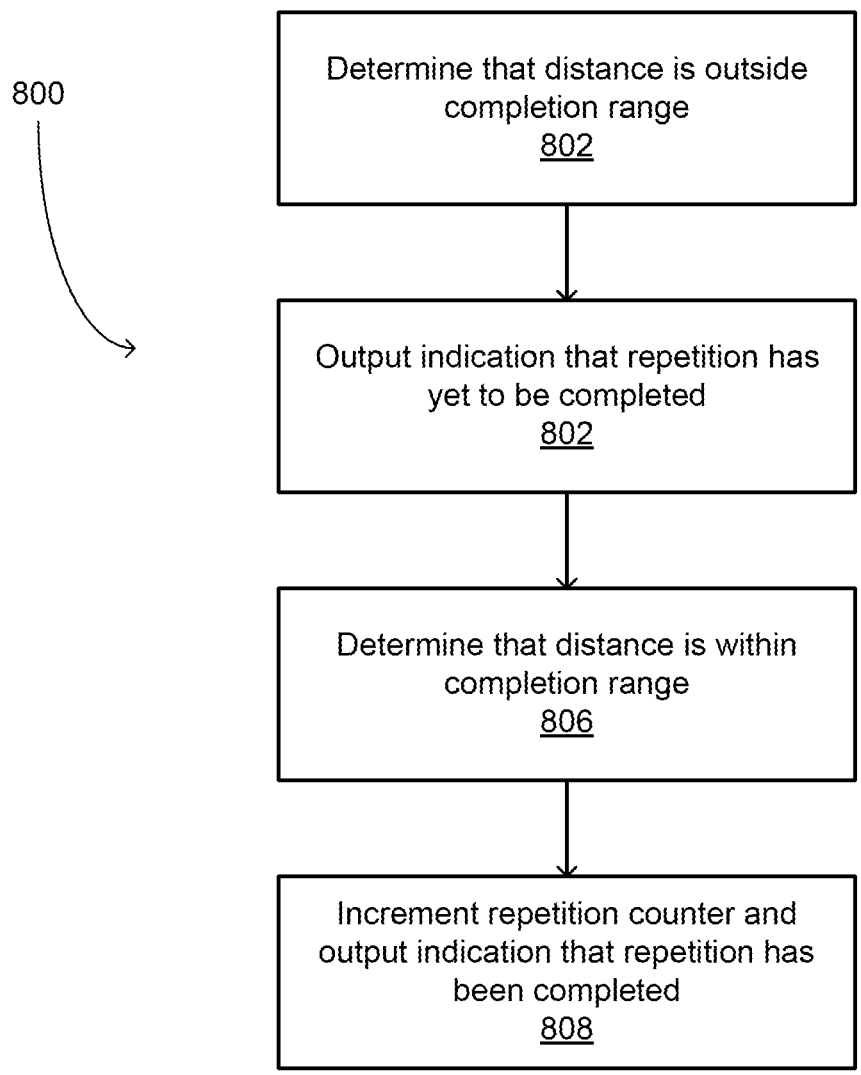
FIG. 8 is a flowchart showing another method performed by the head-mounted device.

FIG. 8 is a flowchart showing another method 800 performed by the head-mounted device 100. The method 800 can include determining, by a head-mounted device 100 based on first data received from a depth-sensing device (such as a camera 602) included in the head-mounted device 100, that a first distance 106 of the head-mounted device 100 from a landmark 104 is outside a completion range 205 (802). The method 800 can include outputting, based on the determination that the first distance 106 of the head-mounted device 100 from the landmark 104 is outside the completion range 205 from the landmark 104, an indication that a repetition has yet to be completed (802). The method 800 can include determining, based on second data received from the depth-sensing device, that a second distance 106 of head-mounted device 100 from the landmark 104 is within the completion range 205 (806). The method 800 can include, based on the determination that the second distance 106 of the head-mounted device 100 from the landmark 104 is within the completion range 205, incrementing a repetition counter 628 and outputting an indication that the repetition has been completed (808).

In some examples, the method 800 can further include determining the completion range 205 based on a height 302, 304 of a user 150 wearing the head-mounted device 100.

In some examples, the method 800 can further include determining the height 302, 304 of the user 150 based on receiving input from the user 150.

In some examples, the method 800 can further include determining the height 302, 304 of the user 150 based on third data received from the depth-sensing device while the user 150 is in a standing position and orientation 110 data received from a gyroscope 604.

In some examples, the method 800 can further include determining an orientation range based on the first distance 106 of the head-mounted device 100 from the landmark 104, determining that an orientation 110 of the head-mounted device 100 is outside the orientation 110 range based on orientation 110 data received from a gyroscope 604, and based on the determination that the orientation 110 of the head-mounted device 100 is outside the orientation, outputting an indication that a form of a user 150 wearing the head-mounted device 100 is incorrect.

In some examples, the method 800 can further include determining an orientation 110 range based on the first distance 106 of the head-mounted device 100 from the landmark 104, determining that an orientation 110 of the head-mounted device 100 is within the orientation 110 range based on orientation data received from a gyroscope 604, and based on the determination that the orientation 110 of the head-mounted device 100 is within the orientation range, outputting an indication that a form of a user 150 wearing the head-mounted device 100 is correct.

Figure 9:
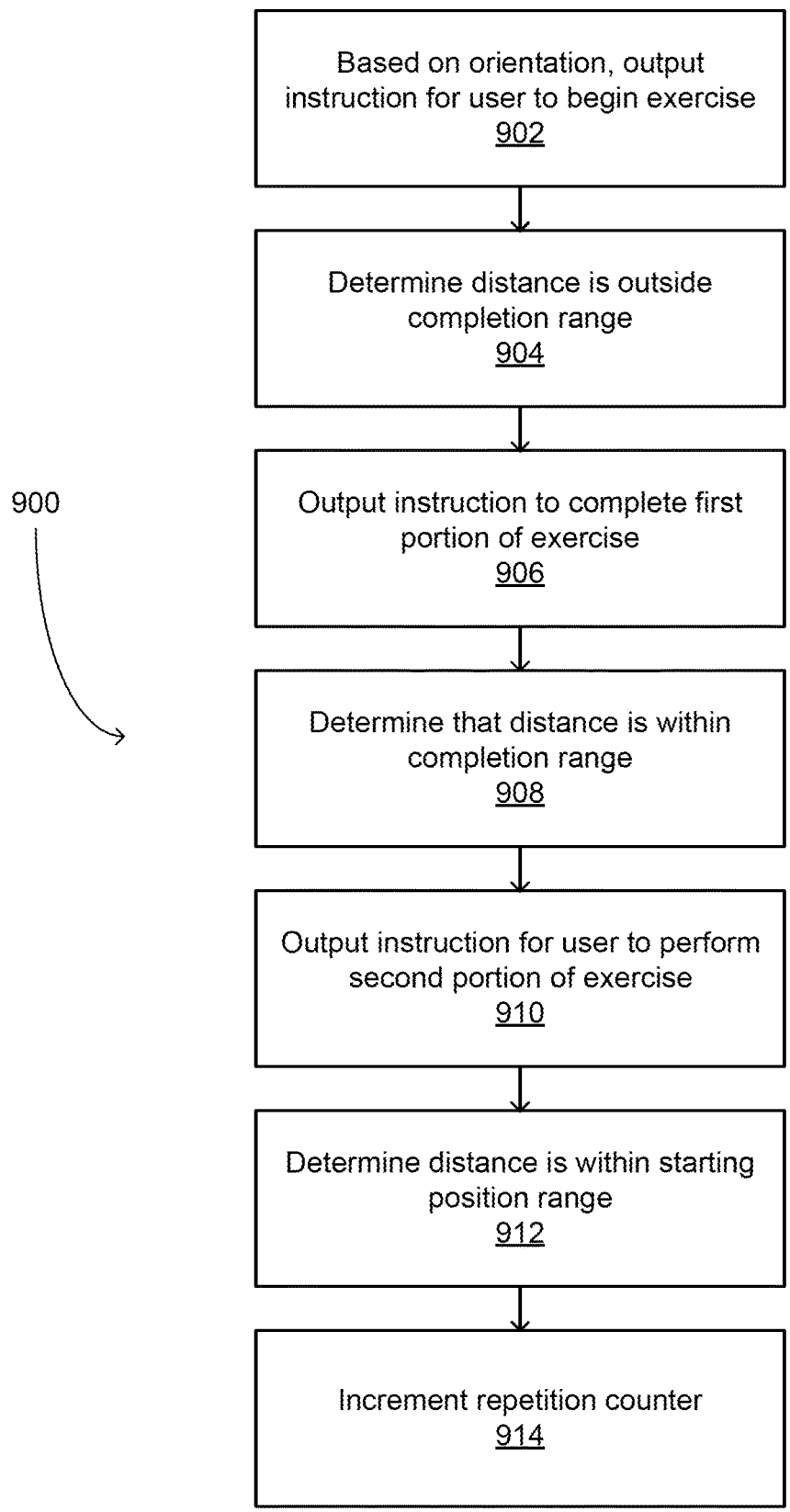
FIG. 9 is a flowchart showing another method performed by the head-mounted device.

FIG. 9 is a flowchart showing another method 900 performed by the head-mounted device 100. The method 900 can include, based on the orientation 110 of the head-mounted device 100 being within a starting orientation range, outputting an instruction for a user 150 to begin an exercise (902). The method 900 can include determining, based on first data captured by the depth-sensing device (such as a camera 602), that a first distance 106 of the head-mounted device 100 from a landmark 104 is outside a completion range 205 (904). The method 900 can include, based on the first distance 106 from the landmark 104 being outside the completion range 205, outputting an instruction for the user 150 to complete a first portion of the exercise (906). The method 900 can include determining, based on second data captured by the depth-sensing device, that a second distance 106 of the head-mounted device 100 from the landmark 104 is within the completion range 205 (908). The method 900 can include, based on the second distance 106 of the head-mounted device 100 from the landmark 104 being within the completion range 205, output an instruction for the user 150 to perform a second portion of the exercise (910). The method 900 can include determining, based on third data captured by the depth-sensing device, that a third distance 106 of the head-mounted device 100 from the landmark 104 is within a starting position range 202 (912). The method 900 can include, based on the third distance 106 of the head-mounted device 100 from the landmark 104 being within the starting position range 202, incrementing a repetition counter 628 (914).

In some examples, the method 900 can further include, before determining that the first distance 106 of the head-mounted device 100 from the landmark 104 is outside the completion range 205 (904), determining, based on fourth data captured by the depth-sensing device, that a third distance 106 of the head-mounted device 100 from the landmark 104 is within the starting position range 202, and based on the determination that the third distance 106 of the head-mounted device 100 from the landmark 104 is within the starting position range 202, setting the repetition counter 628 to zero.

In some examples, the method 900 can further include, after outputting the instruction for the user 150 to begin the exercise (902), running a timer 632 while the third distance 106 of the head-mounted device 100 from the landmark 104 is within the starting position range 202, and outputting a value of the timer 632.

In some examples, the method 900 can further include, after outputting the instruction for the user 150 to begin the exercise (902), determining that the orientation 110 of the head-mounted device 100 is outside a proper form range, the proper form range being based on the first distance 106 of the head-mounted device 100 from the landmark 104, and based on the determination that the orientation 110 of the head-mounted device 100 is outside the proper form range, outputting an instruction for the user 150 to correct a body posture of the user 150.

In some examples, the completion range 205 can be based on a height 302, 304 of the user 150.

In some examples, the method 900 can further include, before outputting the instruction for the user 150 to begin the exercise (902), determining the height 302, 304 of the user 150 based on fourth data captured by the depth-sensing device.

In some examples wherein the completion range 205 is based on a height 302, 304 of the user 150 and a category of the exercise.

In some examples, the method 900 can further include determining that a speed of the head-mounted device 100 exceeded a speed threshold, and based on the speed of the head-mounted device 100 exceeding the speed threshold, outputting an instruction for the user 150 to slow a performance of the exercise.

In some examples, the landmark 104 can include a portion of a surface 102 on which the user 150 is performing the exercise.

Figure 10:
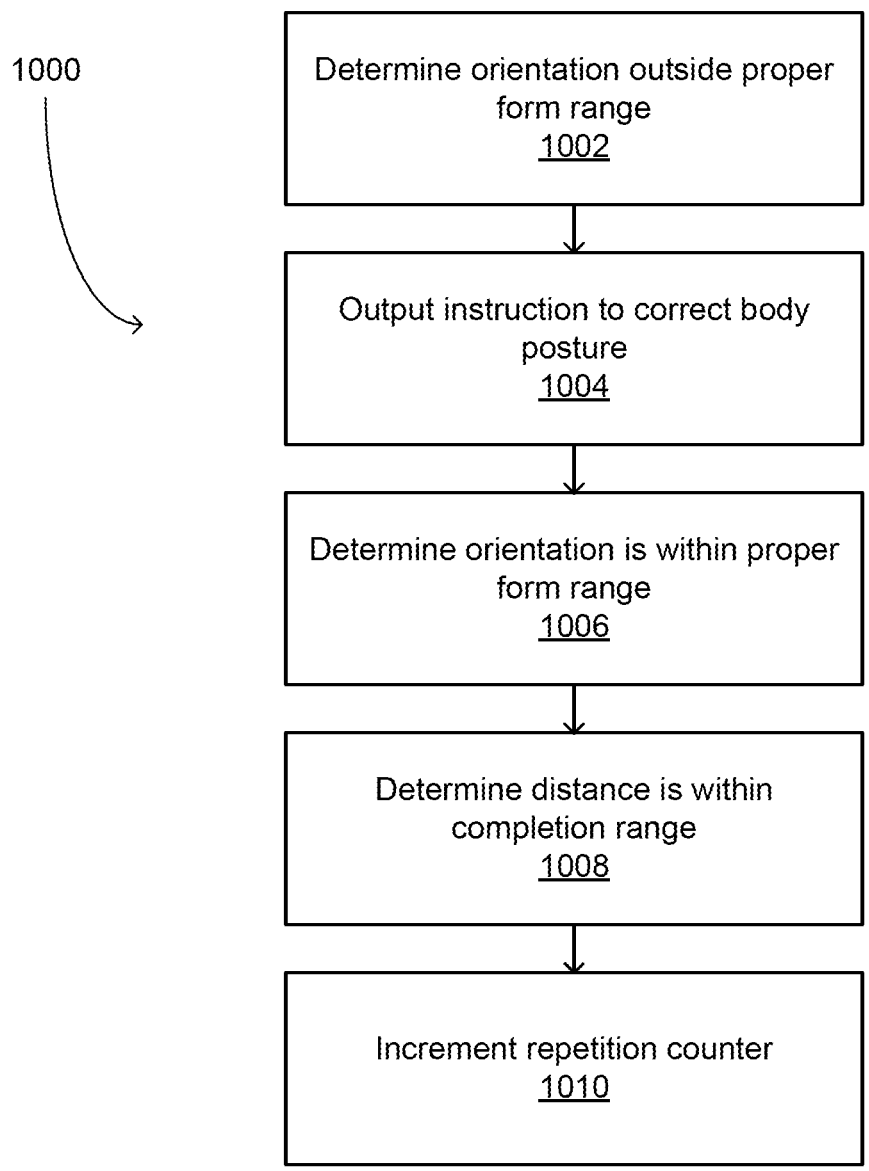
FIG. 10 is a flowchart showing another method performed by the head-mounted device.

FIG. 10 is a flowchart showing another method 1000 performed by the head-mounted device 100. The method 1000 can include determining that a first orientation 110 of the head-mounted device 100 is outside a proper form range (1002), the proper form range being based on a distance 106 of the head-mounted device 100 from a landmark 104. The method 1000 can include, based on the determination that the first orientation 110 of the head-mounted device 100 is outside the proper form range (1002), outputting an instruction for a user 150 to correct a body posture of the user 150 (1004). The head-mounted device 100 can be mounted on a head of the user 150. The method 1000 can include determining that a second orientation 110 of the head-mounted device 100 is within the proper form range (1006). The method 1000 can include determining, based on data received from a depth-sensing device (such as a camera 602) and after the determination that the second orientation 110 of the head-mounted device 100 is within the proper form range (1006), that a distance 106 of the head-mounted device 100 from a landmark 104 is within a completion range 205 (1008). The method 1000 can include, based on the distance 106 of the head-mounted device 100 from the landmark 104 being within the completion range 205, incrementing a repetition counter 628 (1010).

In some examples, the method 1000 can further include, based on the distance 106 of the head-mounted device 100 from the landmark 104 being within the completion range 710, outputting an indication that a repetition has been completed.

In some examples, the method 1000 can further include, based on the determination that the second orientation 110 of the head-mounted device 100 is within the proper form range (1006), outputting an indication that the user 150 is performing an exercise with proper form.

In some examples, the completion range 205 can be based on a height 302, 304 of the user 150.

In some examples, the landmark 104 can include a portion of a surface 102 on which the user 150 is performing an exercise.

Figure 11:
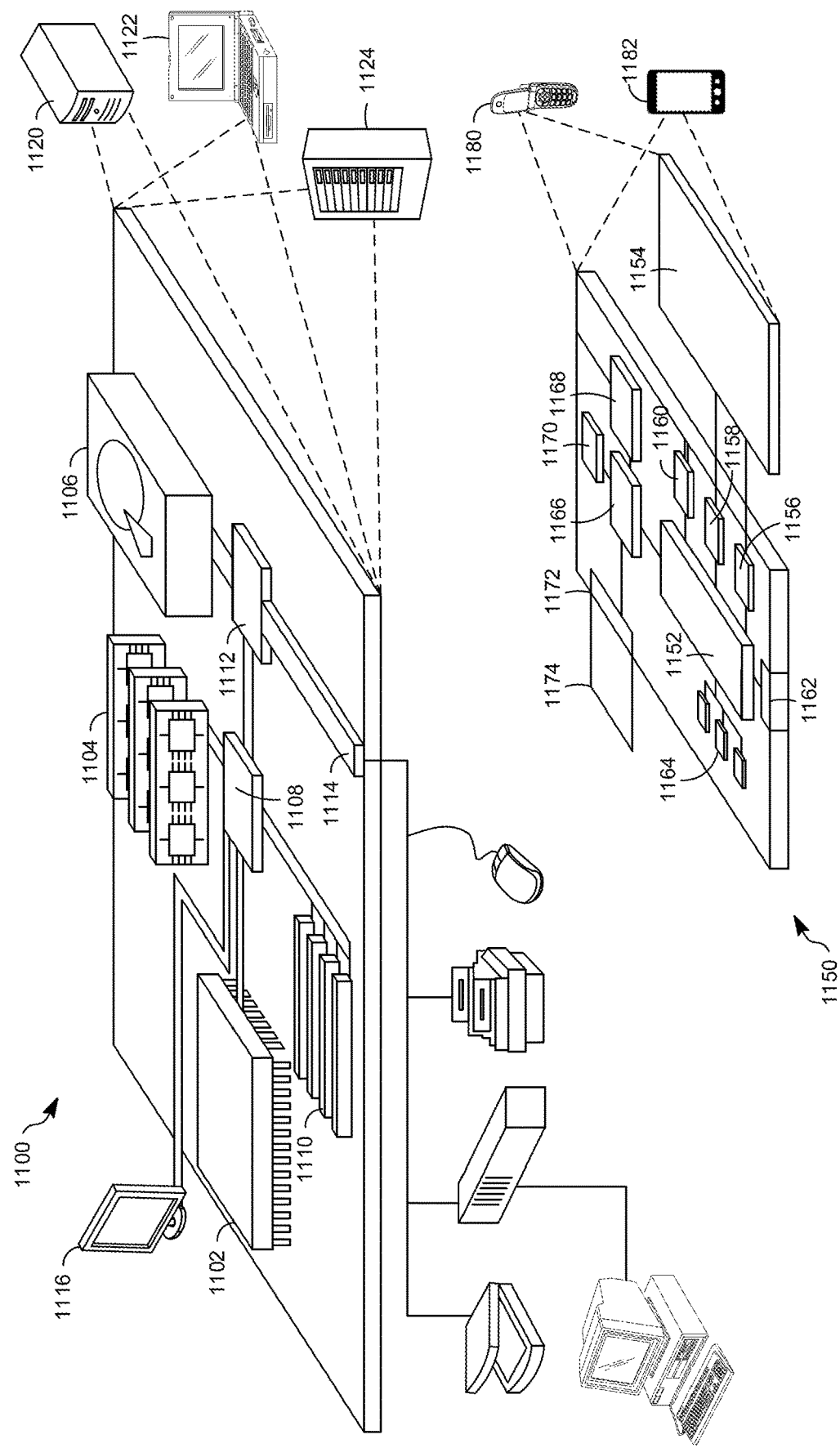
FIG. 11 shows an example of a computer device and a mobile computer device that can be used to implement the techniques described here.

FIG. 11 shows an example of a generic computer device 1100 and a generic mobile computer device 1150, which may be used with the techniques described here. Computing device 1100 is intended to represent various forms of digital computers, such as laptops, desktops, tablets, workstations, personal digital assistants, televisions, servers, blade servers, mainframes, and other appropriate computing devices. Computing device 1150 is intended to represent various forms of mobile devices, such as personal digital assistants, cellular telephones, smart phones, and other similar computing devices. The components shown here, their connections and relationships, and their functions, are meant to be exemplary only, and are not meant to limit implementations of the inventions described and/or claimed in this document.

Computing device 1100 includes a processor 1102, memory 1104, a storage device 1106, a high-speed interface 1108 connecting to memory 1104 and high-speed expansion ports 1110, and a low speed interface 1112 connecting to low speed bus 1114 and storage device 1106. The processor 1102 can be a semiconductor-based processor. The memory 1104 can be a semiconductor-based memory. Each of the components 1102, 1104, 1106, 1108, 1110, and 1112, are interconnected using various busses, and may be mounted on a common motherboard or in other manners as appropriate. The processor 1102 can process instructions for execution within the computing device 1100, including instructions stored in the memory 1104 or on the storage device 1106 to display graphical information for a GUI on an external input/output device, such as display 1116 coupled to high speed interface 1108. In other implementations, multiple processors and/or multiple buses may be used, as appropriate, along with multiple memories and types of memory. Also, multiple computing devices 1100 may be connected, with each device providing portions of the necessary operations (e.g., as a server bank, a group of blade servers, or a multi-processor system).

The memory 1104 stores information within the computing device 1100. In one implementation, the memory 1104 is a volatile memory unit or units. In another implementation, the memory 1104 is a non-volatile memory unit or units. The memory 1104 may also be another form of computer-readable medium, such as a magnetic or optical disk.

The storage device 1106 is capable of providing mass storage for the computing device 1100. In one implementation, the storage device 1106 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 1104, the storage device 1106, or memory on processor 1102.

The high speed controller 1108 manages bandwidth-intensive operations for the computing device 1100, while the low speed controller 1112 manages lower bandwidth-intensive operations. Such allocation of functions is exemplary only. In one implementation, the high-speed controller 1108 is coupled to memory 1104, display 1116 (e.g., through a graphics processor or accelerator), and to high-speed expansion ports 1110, which may accept various expansion cards (not shown). In the implementation, low-speed controller 1112 is coupled to storage device 1106 and low-speed expansion port 1114. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1100 may be implemented in a number of different forms, as shown in the figure. For example, it may be implemented as a standard server 1120, or multiple times in a group of such servers. It may also be implemented as part of a rack server system 1124. In addition, it may be implemented in a personal computer such as a laptop computer 1122. Alternatively, components from computing device 1100 may be combined with other components in a mobile device (not shown), such as device 1150. Each of such devices may contain one or more of computing device 1100, 1150, and an entire system may be made up of multiple computing devices 1100, 1150 communicating with each other.

Computing device 1150 includes a processor 1152, memory 1164, an input/output device such as a display 1154, a communication interface 1166, and a transceiver 1168, among other components. The device 1150 may also be provided with a storage device, such as a microdrive or other device, to provide additional storage. Each of the components 1150, 1152, 1164, 1154, 1166, and 1168, are interconnected using various buses, and several of the components may be mounted on a common motherboard or in other manners as appropriate.

The processor 1152 can execute instructions within the computing device 1150, including instructions stored in the memory 1164. The processor may be implemented as a chipset of chips that include separate and multiple analog and digital processors. The processor may provide, for example, for coordination of the other components of the device 1150, such as control of user interfaces, applications run by device 1150, and wireless communication by device 1150.

Processor 1152 may communicate with a user through control interface 1158 and display interface 1156 coupled to a display 1154. The display 1154 may be, for example, a TFT LCD (Thin-Film-Transistor Liquid Crystal Display) or an OLED (Organic Light Emitting Diode) display, or other appropriate display technology. The display interface 1156 may comprise appropriate circuitry for driving the display 1154 to present graphical and other information to a user. The control interface 1158 may receive commands from a user and convert them for submission to the processor 1152. In addition, an external interface 1162 may be provided in communication with processor 1152, so as to enable near area communication of device 1150 with other devices. External interface 1162 may provide, for example, for wired communication in some implementations, or for wireless communication in other implementations, and multiple interfaces may also be used.

The memory 1164 stores information within the computing device 1150. The memory 1164 can be implemented as one or more of a computer-readable medium or media, a volatile memory unit or units, or a non-volatile memory unit or units. Expansion memory 1174 may also be provided and connected to device 1150 through expansion interface 1172, which may include, for example, a SIMM (Single In Line Memory Module) card interface. Such expansion memory 1174 may provide extra storage space for device 1150, or may also store applications or other information for device 1150. Specifically, expansion memory 1174 may include instructions to carry out or supplement the processes described above, and may include secure information also. Thus, for example, expansion memory 1174 may be provided as a security module for device 1150, and may be programmed with instructions that permit secure use of device 1150. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 1164, expansion memory 1174, or memory on processor 1152, that may be received, for example, over transceiver 1168 or external interface 1162.

Device 1150 may communicate wirelessly through communication interface 1166, which may include digital signal processing circuitry where necessary. Communication interface 1166 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1168. In addition, short-range communication may occur, such as using a Bluetooth, WiFi, or other such transceiver (not shown). In addition, GPS (Global Positioning System) receiver module 1170 may provide additional navigation- and location-related wireless data to device 1150, which may be used as appropriate by applications running on device 1150.

Device 1150 may also communicate audibly using audio codec 1160, which may receive spoken information from a user and convert it to usable digital information. Audio codec 1160 may likewise generate audible sound for a user, such as through a speaker, e.g., in a handset of device 1150. Such sound may include sound from voice telephone calls, may include recorded sound (e.g., voice messages, music files, etc.) and may also include sound generated by applications operating on device 1150.

The computing device 1150 may be implemented in a number of different forms, as shown in the figure. For example, it may be implemented as a cellular telephone 1180. It may also be implemented as part of a smart phone 1182, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the invention.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A method comprising:
   determining, by a head-mounted device based on first depth-sensing data received from a depth-sensing device included in the head-mounted device and first orientation data received from an orientation sensor included in the head-mounted device, that a first distance of the head-mounted device from a landmark is outside a completion range;
   outputting, based on the determination that the first distance of the head-mounted device from the landmark is outside the completion range from the landmark, an indication that a repetition has yet to be completed;
   determining, based on second depth-sensing data received from the depth-sensing device and second orientation data received from the orientation sensor, that a second distance of the head-mounted device from the landmark is within the completion range; and
   based on the determination that the second distance of the head-mounted device from the landmark is within the completion range, incrementing a repetition counter and outputting an indication that the repetition has been completed.

2. The method of claim 1, further comprising determining the completion range based on a height of a user wearing the head-mounted device.

3. The method of claim 2, further comprising determining the height of the user based on receiving input from the user.

4. The method of claim 2, further comprising determining the height of the user based on third depth-sensing data received from the depth-sensing device while the user is in a standing position and the orientation data received from the orientation sensor.

5. The method of claim 1, further comprising:
   determining an orientation range based on the first distance of the head-mounted device from the landmark;
   determining that an orientation of the head-mounted device is outside the orientation range based on the first orientation data received from the orientation sensor; and
   based on the determination that the orientation of the head-mounted device is outside the orientation range, outputting an indication that a form of a user wearing the head-mounted device is incorrect.

6. The method of claim 1, further comprising:
   determining an orientation range based on the first distance of the head-mounted device from the landmark;
   determining that an orientation of the head-mounted device is within the orientation range based on first orientation data received from the orientation sensor; and
   based on the determination that the orientation of the head-mounted device is within the orientation range, outputting an indication that a form of a user wearing the head-mounted device is correct.

7. A head-mounted device comprising:
   a depth-sensing device;
   an orientation sensor configured to determine an orientation of the head-mounted device;
   at least one processor; and
   a non-transitory computer-readable storage medium comprising instructions stored thereon that, when executed by the at least one processor, are configured to cause the head-mounted device to:
      based on the orientation of the head-mounted device being within a starting orientation range, output an instruction for a user to begin an exercise, the head-mounted device being disposed on a head of the user;
      determine, based on first data captured by the depth-sensing device, that a first distance of the head-mounted device from a landmark is outside a completion range;
      based on the first distance from the landmark being outside the completion range, output an instruction for the user to complete a first portion of the exercise;
      determine, based on second data captured by the depth-sensing device, that a second distance of the head-mounted device from the landmark is within the completion range;
      based on the second distance of the head-mounted device from the landmark being within the completion range, output an instruction for the user to perform a second portion of the exercise;
      determine, based on third data captured by the depth-sensing device, that a third distance of the head-mounted device from the landmark is within a starting position range; and
      based on the third distance of the head-mounted device from the landmark being within the starting position range, increment a repetition counter.

8. The head-mounted device of claim 7, wherein the instructions are further configured to cause the head-mounted device to, before determining that the first distance of the head-mounted device from the landmark is outside the completion range:
   determine, based on fourth data captured by the depth-sensing device, that a third distance of the head-mounted device from the landmark is within the starting position range; and
   based on the determination that the third distance of the head-mounted device from the landmark is within the starting position range, set the repetition counter to zero.

9. The head-mounted device of claim 8, wherein the instructions are further configured to cause the head-mounted device to, after outputting the instruction for the user to begin the exercise:
   run a timer while the third distance of the head-mounted device from the landmark is within the starting position range; and
   output a value of the timer.

10. The head-mounted device of claim 7, wherein the instructions are further configured to cause the head-mounted device to, after outputting the instruction for the user to begin the exercise:
 determine that the orientation of the head-mounted device is outside a form range, the form range being based on the first distance of the head-mounted device from the landmark; and
 based on the determination that the orientation of the head-mounted device is outside the form range, output an instruction for the user to correct a body posture of the user.

11. The head-mounted device of claim 7, wherein the completion range is based on a height of the user.

12. The head-mounted device of claim 11, wherein the instructions are further configured to cause the head-mounted device to, before outputting the instruction for the user to begin the exercise, determine the height of the user based on fourth data captured by the depth-sensing device.

13. The head-mounted device of claim 7, wherein the completion range is based on a height of the user and a category of the exercise.

14. The head-mounted device of claim 7, wherein:
 the head-mounted device further comprises an accelerometer; and
 the instructions are further configured to cause the head-mounted device to:
  determine that a speed of the head-mounted device exceeded a speed threshold; and
  based on the speed of the head-mounted device exceeding the speed threshold, output an instruction for the user to slow a performance of the exercise.

15. The head-mounted device of claim 7, wherein the landmark comprises a portion of a surface on which the user is performing the exercise.

16. A non-transitory computer-readable storage medium comprising instructions stored thereon that, when executed by at least one processor, are configured to cause a head-mounted device to:
 determine that a first orientation of the head-mounted device is outside a first form range, the first form range being based on a first distance of the head-mounted device from a landmark;
 based on the determination that the first orientation of the head-mounted device is outside the first form range, output an instruction for a user to correct a body posture of the user, the head-mounted device being mounted on a head of the user;
 determine that a second orientation of the head-mounted device is within a second form range, the second form range being based on a second distance of the head-mounted device from the landmark;
 determine, based on data received from a depth-sensing device and after the determination that the second orientation of the head-mounted device is within the second form range, that a third distance of the head-mounted device from the landmark is within a completion range; and
 based on the third distance of the head-mounted device from the landmark being within the completion range, increment a repetition counter.

17. The non-transitory computer-readable storage medium of claim 16, wherein the instructions are further configured to cause the head-mounted device to, based on the third distance of the head-mounted device from the landmark being within the completion range, output an indication that a repetition has been completed.

18. The non-transitory computer-readable storage medium of claim 16, wherein the instructions are further configured to cause the head-mounted device to, based on the determination that the second orientation of the head-mounted device is within the second form range, output an indication that the user is performing an exercise with proper form.

19. The non-transitory computer-readable storage medium of claim 16, wherein the completion range is based on a height of the user.

20. The non-transitory computer-readable storage medium of claim 16, wherein the landmark includes a portion of a surface on which the user is performing an exercise.

* * * * *